United States Patent
Santerre et al.

(10) Patent No.: US 10,772,992 B2
(45) Date of Patent: Sep. 15, 2020

(54) SOFT TISSUE FILLER

(71) Applicants: THE GOVERNING COUNCIL OF THE UNIVERSITY OF TORONTO, Toronto (CA); UNIVERSITY HEALTH NETWORK, Toronto (CA)

(72) Inventors: Paul Santerre, Toronto (CA); Soror Sharifpoor, Toronto (CA); Wey Liang Leong, Toronto (CA)

(73) Assignees: The Governing Council of the University of Toronto, Toronto (CA); University Health Network, Toronto (CA)

( * ) Notice: Subject to any disclaimer, the term of this patent is extended or adjusted under 35 U.S.C. 154(b) by 99 days.

(21) Appl. No.: 15/999,308

(22) PCT Filed: Feb. 16, 2017

(86) PCT No.: PCT/CA2017/000030
§ 371 (c)(1),
(2) Date: Aug. 17, 2018

(87) PCT Pub. No.: WO2017/139868
PCT Pub. Date: Aug. 24, 2017

(65) Prior Publication Data
US 2019/0038812 A1   Feb. 7, 2019

Related U.S. Application Data

(60) Provisional application No. 62/296,146, filed on Feb. 17, 2016.

(51) Int. Cl.
*A61L 27/58* (2006.01)
*A61L 27/18* (2006.01)
(Continued)

(52) U.S. Cl.
CPC ............... *A61L 27/58* (2013.01); *A61K 9/16* (2013.01); *A61L 27/18* (2013.01); *A61L 27/56* (2013.01);
(Continued)

(58) Field of Classification Search
CPC ...... A61L 17/06; A61L 24/0042; A61L 27/58; A61L 31/148; A61F 2210/0004
(Continued)

(56) References Cited

U.S. PATENT DOCUMENTS 7,494,614 B2 *  2/2009  Pilliar ..................... C04B 38/00
                                                              264/666
8,696,750 B2 *  4/2014  Santerre ................ C07C 59/305
                                                              623/17.11
(Continued)

FOREIGN PATENT DOCUMENTS

CA    2687422 A1   8/2008
CA    2701186 A1   4/2009
(Continued)

OTHER PUBLICATIONS

Anderson JM, Rodriguez A, Chang DT. Foreign body reaction to biomaterials. Semin Immunol 2008;20(2):86-100.
(Continued)

*Primary Examiner* — Suzette J Gherbi
(74) *Attorney, Agent, or Firm* — Norton Rose Fulbright Canada LLP

(57) ABSTRACT

A soft tissue filler comprising a biodegradable amino-acid derived polycarbonate-urethanes and methods of repairing soft tissue defects are provided. The biodegradable soft tissue filler comprises a porous scaffold that is the reaction product of: a) a divinyl oligomer component that comprises a carbonate-derived divinyl oligomer that is the reaction product of a lysine-derived diisocyanate, a vinyl coupling
(Continued)

agent, and a polycarbonate and, optionally, an ether-derived divinyl oligomer, wherein the ether-derived divinyl oligomer is the reaction product of a lysine-derived diisocyanate, a vinyl coupling agent, and an ether; b) at least one anionic monomer; and c) at least one hydrophobic monomer. The molar ratio of (a):(b+c) is between about 1:≥21 and about 1:30, the soft tissue filler has a porosity of >75%; and a compressive moduli of between about 1 kPa and about 50 kPa.

23 Claims, 15 Drawing Sheets

(51) Int. Cl.
  *A61L 27/56* (2006.01)
  *A61K 9/16* (2006.01)
(52) U.S. Cl.
  CPC ....... *A61L 2400/06* (2013.01); *A61L 2430/04* (2013.01)
(58) Field of Classification Search
  USPC ............................................. 623/23.72–23.76
  See application file for complete search history.

(56) References Cited

U.S. PATENT DOCUMENTS

| | | | |
|---|---|---|---|
| 10,045,801 B2* | 8/2018 | Whyne | B32B 13/14 |
| 2002/0071856 A1* | 6/2002 | Dillingham | A61L 27/18 424/427 |
| 2014/0188227 A1* | 7/2014 | Santerre | A61L 27/18 623/17.16 |
| 2017/0232142 A1* | 8/2017 | Santerre | A61K 47/32 514/772.6 |
| 2019/0038328 A1* | 2/2019 | Whyne | A61B 17/80 |

FOREIGN PATENT DOCUMENTS

| | | | |
|---|---|---|---|
| CA | 2681814 A1 | 4/2010 | |
| CA | 2957968 A1 | 2/2016 | |
| WO | 2010142784 A2 | 12/2010 | |
| WO | 2011075183 A1 | 6/2011 | |
| WO | 2016023102 A1 | 2/2016 | |

OTHER PUBLICATIONS

Battiston KG, Labow RS, Simmons CA, Santerre JP. Immunomodulatory polymeric scaffold enhances extracellular matrix production in cell co-cultures under dynamic mechanical stimulation, Acta Biomater, 24, 74-86 (2015).
Cass CA, Burg KJ. Tannic acid cross-linked collagen scaffolds and their anti-cancer potential in a tissue engineered breast implant. J Biomater Sci Polym Ed 2012;23(1-4):281-98.
Cheung JWC, Rose E, Santerre JP. Perfused culture of gingival fibroblasts in a degradable-polar hydrophobic ionic polyurethane (D-PHI) scaffold leads to enhanced proliferation and metabolic activity, Acta Biomaterialia, 9, 6867-6875 (2013).
Churgin S, Isakov R, Yetman R. Reconstruction options following breast conservation therapy. Cleve Clin J Med 2008;75 Suppl 1:S24-9.
Clough KB, Kroll SS, Audretsch W. An approach to the repair of partial mastectomy defects. Plast Reconstr Surg 1999;104(2):409-20.
Clough KB, Lewis JS, Couturaud B, Fitoussi A, Nos C, Falcou MC. Oncoplastic techniques allow extensive resections for breast-conserving therapy of breast carcinomas. Ann Surg 2003;237(1):26-34.
David DJ, Staley HB. Analytical Chemistry of the Polyurethanes: Wiley-Interscience: New York; 1969.
Fisher B, Bauer M, Margolese R, Poisson R, Pilch Y, Redmond C, Fisher E, Wolmark N, Deutsch M, Montague E and others. Five-year results of a randomized clinical trial comparing total mastectomy and segmental mastectomy with or without radiation in the treatment of breast cancer. N Engl J Med 1985;312(11):665-73.
Fisher B, Redmond C, Poisson R, Margolese R, Wolmark N, Wickerham L, Fisher E, Deutsch M, Caplan R, Pilch Y and others. Eight-year results of a randomized clinical trial comparing total mastectomy and lumpectomy with or without irradiation in the treatment of breast cancer. N Engl J Med 1989;320(13):822-8.
Fisher B, Anderson S, Redmond CK, Wolmark N, Wickerham DL, Cronin WM. Reanalysis and results after 12 years of follow-up in a randomized clinical trial comparing total mastectomy with lumpectomy with or without irradiation in the treatment of breast cancer. N Engl J Med 1995;333(22)1456-61.
Gentile P, Di Pasquali C, Bocchini I, Floris M, Eleonora T, Fiaschetti V, Floris R, Cervelli V. Breast Reconstruction With Autologous Fat Graft Mixed With Platelet-Rich Plasma. Surg Innov 2012.
Gruber S, Whitworth AB, Kemmler G, Papp C. New risk factors for donor site seroma formation after latissimus dorsi flap breast reconstruction: 10-year period outcome analysis. J Plast Reconstr Aesthet Surg 2011;64(1):69-74.
Huemer GM, Schrenk P, Moser F, Wagner E, Wayand W. Oncoplastic techniques allow breast-conserving treatment in centrally located breast cancers. Plast Reconstr Surg 2007;120(2):390-8.
Julian JF, Navines J, Botey M, Pascual I, Balibrea JM, Fernandez-Llamazares J, Grifols JR, Mariscal A. [Use of platelet gel in breast reconstruction after breast-conserving cancer surgery]. Cir Esp 2012;90(9):582-8.
Kijima, Yuko et al. Immediate breast reconstruction using autologous free dermal fat grafts provides better cosmetic results for patients with upper inner cancerous lesions. Surg Today 2011;41(4):477-89.
Knonop J, Tran Cao H, Tokin C, Malcame V, Blair S. 152C: Immediate Partial Breast Reconstruction Following Lumpectomy or Partial Mastectomy Using Acellular Dermal Matrix (Alloderm): Outcomes Study Initial Experience. Plast Reconstr Surg 2010;125(6):102.
Kronowitz SJ, Feledy JA, Hunt KK, Kuerer HM, Youssef A, Koutz CA, Robb GL. Determining the optimal approach to breast reconstruction after partial mastectomy. Plast Reconstr Surg 2006;117(1):1-11; discussion 12-4.
Lee J, Bae Y, Audretsch W. Combination of two local flaps for large defects after breast conserving surgery. Breast 2012;21(2)194-8.
Loh QL, Choong C. Three-dimensional scaffolds for tissue engineering applications: role of porosity and pore size. Tissue Eng Part B Rev 2013;19(6):485-502.
McBane JE, Matheson LA, Sharifpoor S, Santerre JP, Labow RS. Effect of polyurethane chemistry and protein coating on monocyte differentiation towards a wound healing phenotype macrophage. Biomaterials 2009;30(29):5497-504.
McBane JE, Sharifpoor S, Kuihua C, Labow RS, Santerre JP, Biodegradation and in vivo biocompatibility of a degradable polar/hydrophobic/ionic polyurethane for use in vascular tissue engineering, Biomaterials, 32, 6034-44 (2011).
McBane JE, Battiston KG, Wadhwani A, Sharifpoor S, Labow RS, Santerre JP, The effect of degradable polymer surfaces on co-cultures of monocytes and smooth muscle cells, Biomaterials, 32, 3584-95 (2011).
McDonald S, Matheson LA, McBane JE, Kuraitis D, Suuronen EJ, Santerre JP, Labow RS, Use of monocyte/endothelial cell co-cultures (in vitro) and a subcutaneous implant mouse model (in vivo) to evaluate a degradable, polar, hydrophobic, ionic polyurethane. J Cell Biochem, 112, 3762-2772 (2011).
Missana MC, Laurent I, Barreau L, Balleyguier C. Autologous fat transfer in reconstructive breast surgery: indications, technique and results. Eur J Surg Oncol 2007;33(6):685-90.
Munhoz AM, Montag E, Arruda EG, Aldrighi C, Gemperli R, Aldrighi JM, Ferreira MC. Critical analysis of reduction mammaplasty techniques in combination with conservative breast surgery for early breast cancer treatment. Plast Reconstr Surg 2006;117(4):1091-103; discussion 1104-7.
Nakamura S, Ishihara M, Takikawa M, Murakami K, Kishimoto S, Nakamura S, Yanagibayashi S, Kubo S, Yamamoto N, Kiyosawa T.

(56) References Cited

OTHER PUBLICATIONS

Platelet-rich plasma (PRP) promotes survival of fat-grafts in rats. Ann Plast Surg 2010;65(1)101-6.
Oh DS, Cheon YW, Jeon YR, Lew DH. Activated platelet-rich plasma improves fat graft survival in nude mice: a pilot study. Dermatol Surg 2011;37(5):619-25.
Perez-Cano R, Vranckx JJ, Lasso JM, Calabrese C, Merck B, Milstein AM, Sassoon E, Delay E, Weiler-Mithoff EM. Prospective trial of adipose-derived regenerative cell (ADRC)-enriched fat grafting for partial mastectomy defects: the RESTORE-2 trial. Eur J Surg Oncol 2012;38(5):382-9.
Piper M, Peled AW, Sbitany H. Oncoplastic breast surgery: current strategies. Gland Surg 2015;4(2):154-63.
Pires Fraga MF, Nishio RT, Ishikawa RS, Perin LF, Helene A, Jr., Malheiros CA. Increased survival of free fat grafts with platelet-rich plasma in rabbits. J Plast Reconstr Aesthet Surg 2010;63(12):e818-22.
Rinker B. The use of dermal autograft as an adjunct to breast reconstruction with tissue expanders. Plast Reconstr Surg 2012;130(6):1179-85.
Salgarello M, Visconti G, Rusciani A. Breast fat grafting with platelet-rich plasma: a comparative clinical study and current state of the art. Plast Reconstr Surg 2011;127(6):2176-85.
Sharifpoor S, Labow RS, Santerre JP. Synthesis and characterization of degradable polar hydrophobic ionic polyurethane scaffolds for vascular tissue engineering applications. Biomacromolecules 2009;10(10)2729-39.
Sharifpoor S, Simmons CA, Labow RS, Santerre JP. A study of vascular smooth muscle cell function under cyclic mechanical loading in a polyurethane scaffold with optimized porosity. Acta Biomater 2010;6(11):4218-28.
Sharifpoor S, Simmons CA, Labow RS, Santerre JP, Functional characterization of human coronary artery smooth muscle cells under cyclic mechanical strain in a degradable polyurethane scaffold, Biomaterials, 32, 4816-29 (2011).
Spear SL, Wilson HB, Lockwood MD. Fat injection to correct contour deformities in the reconstructed breast. Plast Reconstr Surg 2005;116(5):1300-5.
Tran Cao HS, Tokin C, Konop J, Ojeda-Fournier H, Chao J, Blair SL. A preliminary report on the clinical experience with AlloDerm in breast reconstruction and its radiologic appearance. Am Surg 2010;76(10):1123-6.
Yang L, Hong J, Wang J, Pilliar RM, Santerre JP. Influence of anionic monomer content on the biodegradation and toxicity of polyvinyl-urethane carbonate-ceramic interpenetrating phase composites. Biomaterials 2005;26(30):5951-9.
Battiston KG, Labow RS, Santerre JP, Protein binding mediation of biomaterial-dependent monocyte activation on a degradable polar hydrophobic ionic polyurethane, Biomaterials, 33, 8316-8328 (2012).
Battiston KG, Ouyang B, Labow RS, Simmons CA, Santerre JP, Monocyte/macrophage cytokine activity regulates vascular smooth muscle cell function within a degradable polyurethane scaffold, Acta Biomater, 10, 1146-55 (2014).
Battiston KG, Ouyang B, Honarparvar E, Qian J, Labow RS, Simmons CA, Santerre JP, Interaction of a block-co-polymeric biomaterial with immunoglobulin G modulates human monocytes towards a non-inflammatory phenotype, Acta Biomater, 24, 35-43 (2015).
Cheung JW, McCulloch CA, Santerre JP, Establishing a gingival fibroblast phenotype in a perfused degradable polyurethane scaffold: mediation by TGF-$\beta$1, FGF-2, $\beta$1-integrin, and focal adhesion kinase, Biomaterials, 35, 10025-32 (2014).
Cheung JW, Jain D, McCulloch CA, Santerre JP, Pro-angiogenic character of endothelial cells and gingival fibroblasts cocultures in perfused degradable polyurethane scaffolds, Tissue Eng Part A, 21, 1587-99 (2015).
Mathieu E, Battiston KG, McBane JE, Davidson L, Suuronen EJ, Santerre JP, Labow RS, Characterization of degradable polar hydrophobic ionic polyurethane with circulating angiogenic cells in vitro. J Biomater Sci Polym Ed, 25, 1159-73 (2014).
McBane JE, Ebadi D, Sharifpoor S, Labow RS, Santerre JP, Differentiation of monocytes on a degradable, polar-hydrophobic-ionic polyurethane: 2-dimensional films versus 3-dimensional scaffolds, Acta Biomaterialia, 7: 115-122 (2011).
McBane JE, Kuihua C, Labow RS, and Santerre JP, Co-culturing monocytes with smooth muscle cells improves cell distribution within a degradable polyurethane scaffold and reduces inflammatory cytokines, Acta Biomaterialia, 8, 488-501 (2012).

\* cited by examiner

Study #1
75% porosity, a:(b+c)=1:20, large pellets

Study #2
80% porosity, a:(b+c)=1:21, small pellets

SOFT TISSUE FILLER

RELATED APPLICATIONS

This application claims priority to U.S. Provisional Patent Application No. 62/296,146, filed on Feb. 17, 2017.

TECHNICAL FIELD

This patent application relates to soft tissue fillers.

BACKGROUND OF THE ART

Soft tissue fillers for connective and/or fatty soft tissues are used in both medical and cosmetic applications to correct various soft tissue defects or to enhance appearance. Soft tissue defects may be caused by various conditions such as soft tissue tumor resection, congenital abnormalities, trauma and aging.

Various compounds have been used as soft tissue fillers, including hyaluronic acid, collagen, as well as biosynthetic polymers, e.g., poly-L-lactic acid, calcium hydroxylapatite, and polymethylmethacrylate, in addition to implants, such as silicone-based implants or using a patients' own fat as a soft tissue filler. Non-limiting examples of various injectable dermal soft tissue fillers commercially available are. hyaluronic acid (e.g. Restylane™ and Juvéderm™); collagen (e.g. Zyderm™, Zyplast™), as well as biosynthetic polymers (e.g. Radiesse™ (calcium hydroxylapatite); Ellansé™ (Polycaprolactone); Sculptra™ (Poly-L-lactic acid). These fillers are commonly injectable. These approaches have various disadvantages. Natural materials can have problems with sourcing and control and consistency of materials. Shaped implants must be pre-sized and do not have the flexibility provided by other fillers, such as e.g. injectable fillers. The use of a patients' own tissue can further complicate surgical procedures and may be associated with higher post-operative complications. Additionally, where the soft tissue fillers are used to address medical concerns, cosmetic concerns are often not adequately addressed by these soft tissue fillers.

One area where poor cosmetic results are particularly problematic is treatment following repair of breast tissue defects arising as a result of breast cancer or the treatment thereof.

Breast cancer is the most commonly diagnosed cancer and the second leading cause of cancer deaths in Canadian women. Approximately, 25,000 Canadian women were diagnosed with breast cancer in 2015 (Canadian Cancer Society), accounting for 26% of all new cancer cases. After several randomized controlled trials confirming the safety and efficacy of breast conserving surgery (BCS) with radiation, it has replaced mastectomy as the most common surgical procedure for breast cancer. Due to improved treatments, most breast cancer survivors are now expected to have a long life expectancy with a good quality of life. However, poor cosmesis and irregular soft tissue defects are commonly observed in patients that undergo BCS. While impairing the patients' aesthetic appearance, soft tissue defects are a main source of psychological distress, emphasizing the increasing need for correction/restoration techniques to address these cosmetic issues. Since commercially-available synthetic implants are fabricated in pre-determined sizes, they are not suitable to reconstruct partial breast deformities of varying sizes and are solely used for full breast reconstruction in post-mastectomy settings.

Several surgical techniques have been explored to address this unmet need. For example, there are a number of oncoplastic surgical techniques available such as local tissue rearrangement, contralateral breast reduction and flap procedures. However, high rates of complications and cost (long operative time and hospital stay) are drawbacks. Local tissue rearrangement, while demonstrating lower complications rates and more cosmetically-acceptable results, is not suitable for patients who have fatty breasts and insufficient breast tissue after resection. Furthermore, in order to achieve symmetry, up to 40% of these patients will require a contralateral breast reduction, consequently increasing the overall surgery time and complications for both breasts. Tissue rearrangement can also complicate revisions of positive surgical margins when needed. This may lead to the decision of performing a mastectomy due to the inability to ascertain the involved margins accurately. Pedicle flap procedures (e.g., latissimus dorsi flap) are recommended for patients with small breasts or significant tissue loss. Advantages of this reconstruction technique are the lack of need for contralateral breast reduction as well as the surgeon's ability to be more aggressive with breast tissue resection without cosmetic detriment. However, extensive surgical dissection, long surgery and recovery time, donor site complications, high costs as well as aesthetic limitations due to potential differences in skin color and texture are main drawbacks of flap procedures.

Autologous fat transfer has also been used to fill the breast defect after BCS. However, this technique offers a temporary solution due to cytosteatonecrosis. More recent reconstruction methods include the use of adipose-derived regenerative cell (ADRC)-enriched fat grafts (Cytori Therapeutics Inc.), platelet-rich plasma (PRP) fat grafts, PRP gels or dermal grafts (Alloderm, LifeCell Corp.), which have shown improved cosmetic outcomes. However, these techniques are in their infancy.

There remains a need for improved and/or alternate methods for partial breast reconstructions and soft tissue fillers.

BRIEF SUMMARY

The present disclosure provides a biodegradable soft tissue filler comprising a porous scaffold that is the reaction product of:

a) a divinyl oligomer component that comprises a carbonate-derived divinyl oligomer that is the reaction product of a lysine-derived diisocyanate, a vinyl coupling agent, and a polycarbonate and, optionally, an ether-derived divinyl oligomer, wherein the ether-derived divinyl oligomer is the reaction product of a lysine-derived diisocyanate, a vinyl coupling agent, and an ether; b) at least one anionic monomer; and c) at least one hydrophobic monomer. The molar ratio of (a):(b+c) is between about 1:21 and about 1:30, the soft tissue filler has a porosity of >75%; and a compressive moduli of between about 1 kPa and about 50 kPa.

In one embodiment, the anionic monomer may be methacrylic acid and/or the hydrophobic monomer is methyl methacrylate.

In one embodiment, component (a) is a carbonate-derived divinyl oligomer and (a), (b) and (c) are reacted in the presence of at least one porogen (d) and (a), (b) and (c) combined comprise between about 5 wt % and 20 wt % of the reaction mixture and (d) comprises between ≥80 and about 95 by wt % of the reaction mixture.

In another embodiment, the divinyl oligomer component comprises the carbonate-derived divinyl oligomer and the ether-derived divinyl oligomer. In this embodiment, (a), (b) and (c) may be reacted in the presence of at least one porogen (d) and (a), (b) and (c) combined comprise between about 5 wt % up to 25 wt % of the reaction mixture and (d) comprises between >75 to about 95 by wt % of the reaction mixture. In one embodiment, (d) comprises between ≥80 and about 95 by wt % of the reaction mixture. The molar ratio of the carbonate-derived divinyl oligomer to ether-derived divinyl oligomer is suitably between about 1:100 to 50:50, preferably about 10:90.

In one embodiment, the soft tissue fillers as described above have a compressive moduli of between about 10 kPa and about 40 kPa.

In various embodiments, the soft tissue fillers as described above demonstrate a swelling of between about 100% and about 300%, 150% to 300%, and more preferably between about 200% and about 250%.

The soft tissue fillers may include one or more additives selected from antioxidants, cross-linkers, plasticizers or nucleating agents.

The soft tissue fillers may be in the form of a pellet. The pellet may have a dry volume of between 0.1 $mm^3$ and 100 $mm^3$, preferably between 1 $mm^3$ and 75 $mm^3$, more preferably 50-60 $mm^3 \pm 10$ $mm^3$.

The soft tissue filler may further include one or more of a therapeutic agent, a bioactive agent and cells.

In one embodiment, the soft tissue filler is injectable.

In one embodiment, the soft tissue filler is a breast tissue filler.

Also provided is a method of repairing a soft tissue defect in a patient in need thereof comprising implanting a soft tissue filler as described above at the site of the soft tissue defect. The method may further include hydrating the soft tissue filler prior to implantation.

The soft tissue defect may be in connective and/or fatty and/or fibrous soft tissue.

In one embodiment, the soft tissue defect is in the breast, and may be the result of a lumpectomy or breast tissue biopsy.

Also provided is a soft tissue filler comprising an amino-acid derived biodegradable polycarbonate-urethane scaffold having a porosity of between about 80% and about 95%, a compressive moduli of between about 1 kPa and about 50 kPa, a swelling capacity of between about 100% and about 300%, and a dry volume of 50 $mm^3 \pm 25$ $mm^3$.

BRIEF DESCRIPTION OF THE DRAWINGS

These and other features of the preferred embodiments of the invention will become more apparent in the following detailed description in which reference is made to the appended drawings wherein.

DETAILED DESCRIPTION

Figure 1:
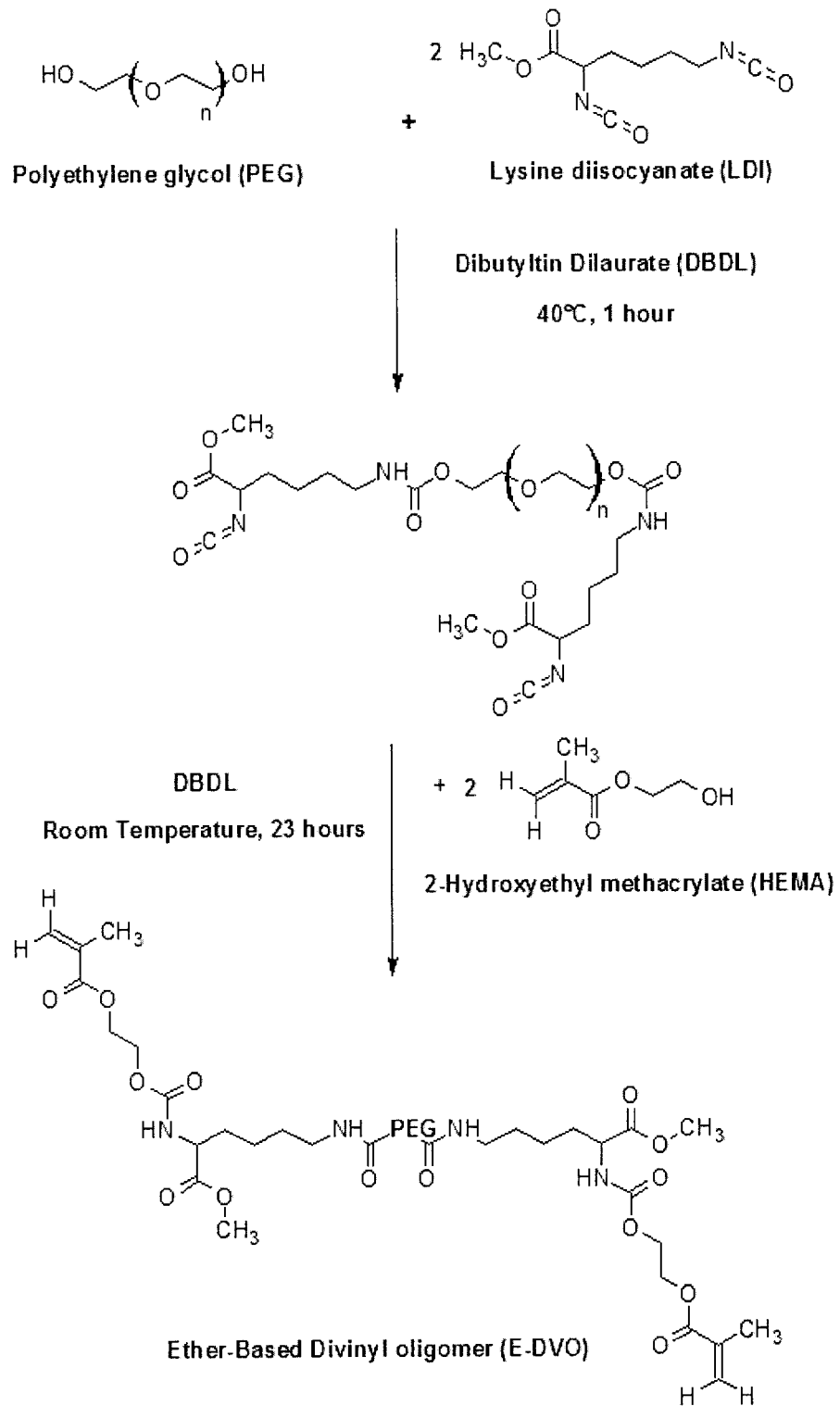
FIG. 1 shows a synthesis scheme of ether-based divinyl oligomer (E-DVO) in the presence of Dibutyltin Dilaurate (DBDL) catalyst.

According to medical dictionaries, soft tissues are any non-calcified tissues in the body. In one embodiment, soft tissues refer to connective and/or fatty and/or fibrous soft tissues. In one embodiment, soft tissues refer in particular to sub-epidermal fatty and/or fibrous tissues. Suitably, the soft tissue fillers described herein are used as fillers for soft tissue that do not form part of a vital organ (heart, brain, lungs, kidneys, liver etc.).

The present disclosure provides amino-acid derived biodegradable polycarbonate-urethane formulations synthesized as soft tissue fillers. In one embodiment, their use is not particularly restricted, and may include, without being limited to, the repair of any soft tissue. Further, the soft tissue fillers described herein may be used for the correction of various soft tissue defects caused by various medical conditions such as soft tissue tumor resection, congenital abnormalities, trauma and aging. The soft tissue fillers may also be used for cosmetic purposes, such as for the enhancement of facial features, such as cheeks or lips.

Soft tissue tumor resection is a common cause of soft tissue defects and, in one embodiment, the soft tissue fillers as described herein may be used for the repair of any soft tissue defect caused by tumour resection with or without a portion of the surrounding tissue. Soft tissue tumor resection includes treatment related to melanoma, where a skin graft may be used on top of a soft tissue filler described herein. Soft tissue defects may also be caused by biopsies. In one embodiment, the defect may be primarily to or in sub-epidermal fatty and/or fibrous tissue.

In one embodiment, soft tissue fillers as described herein may be used the repair of breast tissue defects following lumpectomy (BCS) or biopsies related to breast cancer.

In one embodiment, the swelling and mechanical properties of the soft tissue fillers are of particular importance and the amino-acid derived biodegradable polycarbonate-urethane fillers were synthesized with swelling and mechanical properties dependent on both the soft segment composition, the porogen content and the size of the soft tissue filler.

In one embodiment, the reaction product has a compressive moduli of at least about 1 kPa but less than about 50 kPa.

In one embodiment, the fillers are highly porous (>75%, ~80% to 95%, 80-90%, or 80-85% by volume)

Amino-acid derived biodegradable polycarbonate-urethane formulations were fabricated with mechanical properties comparable to that of native healthy breast tissue, which were capable of preserving breast shape/volume upon implantation while eliciting minimal foreign body reaction and integrating well within the host tissue. Due to the segmented nature of PUs, amino-acid derived biodegradable polycarbonate-urethane porous fillers can be fabricated with desirable properties, customized for this specific application.

The soft tissue fillers were synthesized by reacting macromer divinyl oligomers with a hydrophobic monomer, an anionic monomer in admixture with one or more porogens.

In one embodiment, the reaction product is a polar non-ionic hydrophobic amino-acid derived degradable polycarbonate-urethane (AAd-DPCU). AAd-DPCUs are synthetic block copolymers characterized by the presence of a urethane linkage created in a condensation reaction (step-growth polymerization). Generic polyurethanes can be linear, branched, or cross-linked while AAd-DPCUs are specifically cross-linked. AAd-DPCUs are copolymers and contain two repeating segments; a hard segment of the polyurethane (the amino-acid derived isocyanate), which endows the material with mechanical strength and a soft segment (the polyol), which provides flexibility. The soft and hard segments can microphase separate to form soft and hard phases; these phases provide the polymer with both flexibility and strength. The combination of segments manifests itself in the bulk material composition and surface microstructure. The differences in polarity of the hard and soft segments affect the hydrophilic-hydrophobic balance of the material. Furthermore, the soft segments are mobile and will optimize their location to minimize the free energy at the surface of the material. The copolymer structure and the composition and the ratio of its monomers provide a AAd-DPCUs with its unique in vivo properties and biocompatibility.

In one embodiment, the hard segment is derived from a lysine derived diisocyanate and vinyl monomers.

In one embodiment, the isocyanate is not particularly restricted. In one embodiment, the isocyanate has a molecular weight between about 100 and about 1000. In one embodiment, the isocyanate component is one or more of a linear diisocyanate e.g. L-Lysine ethyl ester diisocyanate; Suitable isocyanates can be prepared by methods known to those of skill in the art and are also available from commercial sources, including, for example, ABI Chem, ABCR, A Chemtek, Akos Building Blocks, Alfa Aesar, Aurora Fine Chemicals, Bayer, CHEMOS GmbH, Chem Reagents, Chemtura, FCH Group, Fisher Scientific, Oakwood Chemical, Perstrop, Polysciences, Inc, Sigma-Aldrich, Suzhou Rovathin and SynQuest.

In one embodiment, the diisocyanate is derived from lysine. In one embodiment, the diisocyanate is lysine diisocyanate (LDI).

In one embodiment, the vinyl coupling agent is not particularly restricted and may be any compound comprising a single pendant hydroxyl or primary or secondary amine group that can react with the isocyanate group of the diisocyanate. In one embodiment, the vinyl coupling agent has a molecular weight between about 50 and about 500. The vinyl coupling agent may be, but is not limited to, a vinyl alcohol, an alkyl amine with vinyl groups, a vinyl amine, hydroxypropyl (meth)acrylate, 2,3-dihydroxypropyl (meth) acrylate, 1,4-butanediol monoacrylate, (poly)ethylene glycol mono(meth)acrylate, 3-aminopropyl vinyl ether, and 2-hydroxyethyl methacrylate (HEMA). In one embodiment, the vinyl coupling agent is 2-hydroxyethyl methacrylate (HEMA).

In one embodiment, the soft segment is derived from a polyol. In one embodiment, the polyol is an oligomeric macromolecule containing hydroxyl or amine end groups with low glass transition temperatures. In one embodiment, the polyol comprises a polyether or polycarbonate backbone.

In various embodiments, the soft segment may be derived from polyethylene oxide; polypropylene oxide; polytetramethylene oxide; polyisobutylene; polybutadienes; polyesters; polyethylene adipate; polyanhydrides, polyamides, polytetramethylene adipate; polycaprolactone; polydimethylsiloxane; and polycarbonates.

In one embodiment, the soft segment is derived from a polycarbonate.

In one embodiment, the soft tissue filler is a scaffold comprising the reaction product of a carbonate-based divinyl oligomer (C-DVO), an ether-based divinyl oligomer (E-DVO), at least one anionic monomer and at least one hydrophobic monomer.

In one embodiment, the C-DVO is a reaction product of poly(hexamethylene carbonate) diol (PCN), LDI, and HEMA. In one embodiment, the E-DVO is a reaction product of PEG, LDI, and HEMA.

In one embodiment, the anionic component is not particularly restricted. In one embodiment, the anionic component has a molecular weight between about 50 and about 1000.

In one embodiment, the anionic component is a vinyl monomer with mono acid function such as methacrylic acid, vinyl phosphoric acid or the like; vinyl monomers with di-acids such as itaconic acid, maleic acid or the like; or vinyl monomers with tri-acids such as tricarballylic acid, tricarboxylic acid or the like.

In one embodiment, the anionic component comprises a methacrylic acid derivative; 2-(methacryloyloxy)ethyl phosphate; styrene sulphonic acid; 2(methacryloyloxy)ethyl succinate, [3-(methacryloylamino)propyl]trimethyl ammonium chloride; or 2-(methacryloyloxy)ethyl]trimethylammonium methyl chloride. In one embodiment, the methacrylic acid derivative is an amino-acid derivative. In one embodiment, the anionic component is methacrylic acid.

In one embodiment, the hydrophobic component is not particularly restricted. In one embodiment, the hydrophobic component has a molecular weight between about 50 and about 1000.

In one embodiment, the component is considered to be hydrophobic if when its constituent monomers are polymerized on their own, in the absence of other monomers or additives, it yields an advancing water contact angle measure of greater than about 50, 55, 60 or 65 degrees. In one embodiment, the advancing water contact angle measure is greater than about 65 degrees. Methods of measuring water contact angle are known to those of skill in the art.

In one embodiment, the hydrophobic compound is a non-aromatic.

In one embodiment, the hydrophobic compound does not include a pendant halogen group, e.g. fluorine.

In one embodiment, the hydrophobic component is an alkyl methacrylate, wherein the alkyl chain is linear or branched, saturated or unsaturated, and wherein the number of carbons is less than 12. In one embodiment, the alkyl chain is non-aromatic. In one embodiment, the hydrophobic component is methyl, propyl, butyl, iso-butyl or t-butyl methacrylate. In one embodiment, the hydrophobic compound comprises an aliphatic alkyl side chain. In one embodiment, the hydrophobic component is methyl methacrylate.

In one embodiment, the scaffold is a porous scaffold. While in one embodiment, a single porogen may be used, in other embodiments, two or more porogens may be used to impart both macro-porosity and micro-porosity to the soft tissue fillers. In one embodiment, porogens used are not particularly restricted. In one embodiment, the porogen system is suitably salt particles and PEG. In one embodiment, suitable salt particles are sodium bicarbonate having an average particle size between about 50 and 450 µm are used and PEG of about 600 da to 4000 but preferably 600 to 2000 is used.

There are three main processes used to generate porosity in the scaffolds (1) processes using porogens, (2) processes using solid free-form or rapid prototyping technologies and (3) techniques using woven or non-woven fibers. In the first category, solid materials either in solids or dissolved in solvents, are incorporated with porogens, which could be gases such as carbon dioxide, liquids such as water, polyethylene glycol or the like, or solids such as paraffin, salts, sugar and others. Porogens are removed by sublimation, evaporation, dissolution or melting to leave behind a porous structure in the scaffold. Examples include solvent casting and particulate leaching, gas foaming, freeze-drying and phase separation.

Porous structures can also be manufactured by sequential delivery of material and/or energy needed to bond the materials to preset points in space. Some solid free-form fabrication technologies include laser sintering, stereolithography and 3D printing, and depend on precise delivery of light or heat energy in a scanner system to points of space in the material bed so as to bond or crosslink the materials to give solid structures in an otherwise soluble bed of materials.

In the third category, woven and non-woven fiber structures can be piled together and bonded using thermal energy or adhesives to give a porous meshwork using techniques such as fiber bonding, or fibers can be generated by the electrospinning technique.

The PU scaffolds suitably have a porosity of >75%, ≥80%, between 80 and about 95% or between 80 and 85%. In one embodiment, the PU scaffolds of the soft tissue filler described herein are synthesized in the presence of >75% by weight of porogen, ≥80%, 80-95%, still more preferably 80-85% by volume wt % by weight of porogen, by weight of the reaction products, to yield scaffolds having these porosities.

In various embodiments, the PU scaffolds have a volume of between 0.1 mm$^3$ and 100 mm$^3$, between 1 mm$^3$ and 75 mm$^3$. In one embodiment, 50 mm$^3$≥25 mm$^3$. In one embodiment, 50 mm$^3$≥20 mm$^3$. In one embodiment 50 mm$^3$ 10 mm$^3$. In one embodiment, 50 mm$^3$ 5 mm$^3$.

The scaffolds or particulates are biodegradable. In one embodiment the scaffold or particulate degrades more than 80% in less than 3 months, less than 6 months, in less than 9 months, in less than 1 yr, or in less than 2 yrs.

Amino-acid derived biodegradable polycarbonate-urethane scaffolds were synthesized by reacting two types of divinyl oligomers (DVDs), a carbonate-based DVO (C-DVO) and an ether-based DVO (E-DVO) with methacrylate (MMA), methacrylic acid (MAA) monomers.

Kinetic studies conducted on both the C-DVO and the E-DVO (FIG. 3) demonstrated the full consumption (~100%) of the isocyanate groups within 24 hours. Both the C-DVO and E-DVO had similar hard segment chemistry through the incorporation of LDI and HEMA. LDI was chosen to render the polymer more biocompatible. Unlike traditional PUs, which produce toxic diamines upon degradation, LDI-based PUs' main degradation product is lysine, a naturally occurring amino acid that is abundant in biological systems. HEMA, the second component of the PU hard segment confers crosslinking functionality to the DVO and thus the potential for improved PU mechanical properties. The ester functionality within HEMA also rendered the scaffold more susceptible to hydrolytic degradation. PCN and PEG constituted the soft segment of the C-DVO and E-DVO, respectively. PUs synthesized with polycarbonate soft segments possess a greater tensile strength and elastic modulus when compared to ether-based PUs and, while demonstrating a greater oxidative stability when compared to poly-ether urethanes (PEUs), are susceptible to hydrolytic degradation. PUs with a polyether soft segment have a lower elastic modulus when compared to PUs with a PCN soft segment due to the greater flexibility of ether linkages. While demonstrating a greater hydrolytic stability, PEUs are more prone to oxidative degradation when compared to PCNUs. Incorporating PEG within PCNUs results in greater mass loss due to hydrolytic degradation with increasing PEG content, which can be attributed to the hydrophilic nature of PEG, which increased PU's water absorption and accelerated the degradation of the polymer's hydrolysable linkages. MAA and MMA methacrylate monomers provide favorable non-specific cell adhesive chemistry.

Amino-acid derived biodegradable polycarbonate-urethane scaffolds were synthesized in the presence of different porogen contents (75 wt % or 80 wt % or more, however 80% is preferred). For formulations with the same monomer composition, increasing the porogen content resulted in amino-acid derived biodegradable polycarbonate-urethane scaffolds with a greater porosity, increased polymer swelling and a lower compressive modulus.

In various embodiments, the scaffold has a modulus of at least 1 kPa but less than 50 kPa. In various embodiments, the scaffold has a modulus of at least 10 kPa and less than 40 kPa, less than 30 kPa, or less than 20 kPa.

Increasing the concentration of E-DVO or the salt porogen was shown to decrease the compressive modulus and increase polymer swelling, resulting in the development of PU filler formulations with properties advantageous for use as soft tissue fillers and, in particular, soft tissue fillers for the repair of breast defects. Formulations were synthesized that exhibited a moderate degree of swelling, possessed mechanical properties comparable to native human breast tissue and were successfully used as soft tissue fillers for partial breast reconstruction in a porcine model. While capable of maintaining the shape, volume and natural stiffness of the breast tissue, these PU fillers were shown to support cell, tissue infiltration and neovascularization throughout their structure. Furthermore, they were observed to integrate well within the host tissue and to not elicit foreign body giant cell and fibrous capsule formation, suggesting the absence of chronic inflammation and presence of wound repair. Amino-acid derived biodegradable polycarbonate-urethane fillers may have one or more of the following advantages over known solutions for soft tissue filler applications such as partial breast reconstruction: requiring no biological processing, minimal surgical dissection, no prior knowledge of the defect dimension/shape and a short surgery time (<10 min).

Other attributes of amino-acid derived biodegradable polycarbonate-urethane fillers as described therein include customizability and versatility. Specifically, these PU fillers can be used for varying defect sizes and a prior knowledge of the exact defect dimension/shape is not required. Furthermore, unlike tissue rearrangement techniques, amino-acid derived biodegradable polycarbonate-urethane fillers are not dependent on sufficient tissue being available for rearrangement to fix the defect. In the context of breast reconstruction, this can eliminate the need for contralateral breast reduction to obtain symmetry which is commonly performed in conjunction with tissue rearrangement procedures. Amino-acid derived biodegradable polycarbonate-urethane fillers may also allow surgical oncologists to be more aggressive in removal of tissue and allow the resection of wider surgical margins with less concerns regarding the cosmetic outcomes, potentially reducing the incidence of positive margins and the need for additional surgery. Lastly, the aesthetic attributes of these degradable fillers were evident in their ability in the in vivo model to preserve breast shape/volume while maintaining natural breast stiffness throughout the 36 week implantation period.

Protein adsorption occurs immediately following the implantation of a biomaterial, or contact of body fluids such as blood to a biomaterial. This adsorbed protein layer is composed of bioactive agents that can greatly influence the behavior of cells or other body fluid elements involved in the inflammatory, immune, and foreign body responses. While the adsorbed protein layer interacts with the surface of the biomaterial, the bulk of the material does not interface with biological tissue and so may not be a major determinant in regulating protein adsorption and the subsequent inflammatory response. For this reason, biomaterials, and particularly polymeric biomaterials, can be modified in the bulk phase by the addition of components that can provide stability or mechanical integrity to the material without influencing the implant's interactions with the proteins, cells, and tissue. For polymeric materials these additives include, but are not limited to, antioxidants, fillers, cross-linkers, plasticizers, nucleating agents, and pigments. Accordingly, in one embodiment, the soft tissue filler further includes one or more additives, which in one embodiment, may be selected from antioxidants, fillers, cross-linkers, plasticizers, nucleating agents, and pigments.

In various embodiments, these additives may be present in an amount of less than 50, less than 40, less than 30, less than 20, less than 10, less than 5 or less than 1 percent by weight of the polymeric material.

In one embodiment, a therapeutic or bioactive agent may be added to the material in the bulk phase or may be impregnated or coated onto the scaffold after synthesis.

In one embodiment, the therapeutic agent or bioactive agent may be present in any amount of less than 50, less than 40, less than 30, less than 20, less than 10, less than 5 or less than 1 percent by weight of the polymeric material.

Such therapeutics or bioactive may include, but are not limited to growth factors, peptides, antibodies, enzymes, platelets, glycoproteins, hormones, glycosaminoglycans, nucleic acids, analgesics, cytokines and combinations thereof.

In one embodiment, the soft tissue filler is used in combination with a cytokine or growth factor.

In one embodiment, the soft tissue fillers as disclosed herein are used in combination with cells, including, but not limited to, stem cells with are implanted with the soft tissue filler at the time of tissue repair.

The soft tissue filler as disclosed herein may further be used in combination with both a therapeutic agent and/or bioactive and one or more cells, including, but not limited to stem cells.

In one embodiment, the soft tissue filler scaffold is not coated, impregnated and/or otherwise used with one of the additional components described above.

In one aspect, there are no restrictions on the manner in which the reagents are added to each other to form soft tissue fillers disclosed herein, the temperature, pressure or atmosphere under which the materials are synthesized from the monomer and macromers or the use of the catalysts in the reaction.

In other embodiments, there is provided methods of manufacturing soft tissue fillers as described herein comprising combining: a) a C-DVO and, optionally, an E-DVO; b) an anionic monomer; c) a hydrophobic monomer; and d) a porogen, wherein (a), (b) and (c) combined comprise between about 5 wt % and up to 25 wt % of the reaction mixture and (d) comprises between 75 wt % and about 95 wt % of the reaction mixture. In one embodiment, the method may further include preparing the macromer C-DVO and/or E-DVO. The method can further include curing the reaction product. The method can further include leaching the porogen from the reaction product. The method can further include drying the porous scaffold that results from the leaching step. Methods of forming beads or pellets may include emulsion polymerization, precipitation methods from a solution of organic polymer, of freezing and pulverizing frozen scaffolds.

The ratio of divinyl oligomers to monomers (a:b+c) is at least 1:21 and less than 1:60, less than 1:50, less than 1:40 and preferably less than 1:30. Data from the pilot study showed that a ratio (a:b+c) lower than 1:21, (i.e. 1:20) resulted in scaffolds with a stiffness higher than the one of normal pig breast tissue and was characterised by a slow degradation rate and significantly different properties from the ratio of (a:b+c) of 1:21. In one embodiment, the ratio (a:b+c) is at least 1:21±0.5. In one embodiment, the ratio (a:b+c) is at least 1:21±0.2. In one embodiment, the ratio (a:b+c) is at least 1.21±0.1. In various embodiments, the ratio (a:b+c) is at least 1:21, at least 1:21.1, at least 1:21.2, or at least 1:21.5. Furthermore it is known in the art that the mechanical properties of polyurethane are dependent on the soft segment composition. As the amount of oligomer soft segments decreases in the formulation, e.g., a ratio (a:b+c) higher than 1:30, the mechanical properties of the polyurethane go up resulting in higher modulus materials which would yield outcomes that are not compliant with the natural soft tissue environment being treated.

In one embodiment, the method may further include preparing the macromer C-DVO and/or E-DVO. The method can further include curing the reaction product. The method may further including freezing the reaction product. In one embodiment, the reaction product is cured and then pulverized to form porous particles.

AAd-DPCU can be synthesized by generating a divinyl oligomer by reaction of a diisocyanate with an oligomeric diol and mono-vinyl monomers with pendent hydroxyl or amine groups. The latter is then light or heat polymerized via a free radical polymerization with anionic and/or hydrophobic vinyl monomers in the presence of initiators with light or heat activating initiators. If porogens were included in the mixture, these are then extracted.

In the presence of a catalyst, polar non-ionic macromonomer polyurethanes are created in a nucleophilic addition reaction between an isocyanate and molecules containing hydroxyl (a polyol) or amine functional groups to create a urethane or carbamate linkage.

The synthesis of macromonomer polyurethane can be completed in one or two steps. The one-step process involves a simultaneous reaction of the isocyanate, polyol, and vinyl coupling agent. In the two-step prepolymer process, an excess of diisocyanate is reacted with the polyol to form NCO-terminated prepolymers with isocyanate functionality as an intermediate; this intermediate is then reacted with the vinyl coupling agent to create the final polar non-ionic macromonomer polyurethane. The separation of the process into two steps enables a greater degree of control over the polar non-ionic macromonomer polyurethane structure and consequently, its properties.

The synthesis of macromonomer polyurethanes is also dependent upon a catalyst, the selection of which depends on the final profile of the polyurethane (e.g. gel, foam) and its curing requirements. The two types of catalysts that can be used are metal complexes and amine compounds. DBDL may suitably be used in preparing the macromonomer polyurethanes used in the soft tissue fillers described herein.

Synthesis processes will generally employ initiators and/or retarders and or terminators. In one embodiment, the initiator used is not particularly restricted and will be within the purview of a person skilled in the art. Suitable initiators can be selected e.g. from diacyl peroxides, peroxy esters, dialkyl peroxides, dialkyl peroxydicarbonates, tert-alkylhydroperoxides, and ketone peroxides. Suitable free radical initiators include e.g. dibenzoyl peroxide, diisobutyrul peroxide, t-butyl peracetate, dicumyl peroxide, di-sec-butyperoxydicarbonate, methyl ethyl ketone peroxide, benzoyl peroxide (BPO) (available through Aldrich Chemical Co., Milwaukee, Wis.) and 1,1'-azobis(cyclohexanecarbonitrile). Light curing systems may be used to polymerize the vinyl resins, including but not limited to photopolymerizations initiated with camphorquinone (CQ, initiator) and 2-(dimethylamino) ethyl methacrylate (DMAEM, co-initiator).

Parameter variations provide the controllable aspect in polyurethane synthesis, which can include modifications to the reacting molecules (e.g. chemical composition, molecular weight, symmetry), the processing conditions (e.g. introduction of water, removal of carbon dioxide, active hydrogens), or addition of additives.

Various methods can be employed in preparing scaffolds according to embodiments of the present invention, including nanofiber-self assembly, textile technologies, solvent casting & particulate leaching (SCPL), gas foaming, emulsification/freeze-drying, thermally induced phase separation (TIPS), electrospinning and CAD/CAM technologies, each of which is briefly described below.

Nanofiber Self-Assembly: Molecular self-assembly enables the synthesis of biomaterials with properties similar in scale and chemistry to that of the natural in vivo extracellular matrix (ECM). Moreover, these hydrogel scaffolds have shown superiority in in vivo toxicology and biocompatibility compared to traditional macroscaffolds and animal-derived materials.

Textile technologies: These techniques include all the approaches that have been successfully employed for the preparation of non-woven meshes of different polymers. In particular, non-woven polyglycolide structures have been tested for tissue engineering applications: such fibrous structures have been found useful to grow different types of cells.

Solvent Casting & Particulate Leaching (SCPL): This approach allows for the preparation of porous structures with regular porosity, but with a limited thickness. First, the polymer is dissolved into a suitable organic solvent, then the solution is cast into a mold filled with porogen particles. Such porogen can be an inorganic salt like sodium chloride, crystals of saccharose, gelatin spheres or paraffin spheres. The size of the porogen particles will affect the size of the scaffold pores, while the polymer to porogen ratio is directly correlated to the amount of porosity of the final structure. After the polymer solution has been cast the solvent is allowed to fully evaporate, then the composite structure in the mold is immersed in a bath of a liquid suitable for dissolving the porogen: water in the case of sodium chloride, saccharose and gelatin or an aliphatic solvent like hexane for use with paraffin. Once the porogen has been fully dissolved, a porous structure is obtained.

Gas Foaming: To overcome the need to use organic solvents and solid porogens, a technique using gas as a porogen has been developed. First, disc-shaped structures made of the desired polymer are prepared by means of compression molding using a heated mold. The discs are then placed in a chamber where they are exposed to high pressure $CO_2$ for several days. The pressure inside the chamber is gradually restored to atmospheric levels. During this procedure the pores are formed by the carbon dioxide molecules that abandon the polymer, resulting in a sponge-like structure.

Emulsification/Freeze-drying: This technique does not require the use of a solid porogen like SCPL. First, a synthetic polymer is dissolved into a suitable solvent then water is added to the polymeric solution and the two liquids are mixed in order to obtain an emulsion. Before the two phases can separate, the emulsion is cast into a mold and quickly frozen by means of immersion into liquid nitrogen. The frozen emulsion is subsequently freeze-dried to remove the dispersed water and the solvent, thus leaving a solidified, porous polymeric structure. While emulsification and freeze-drying allow for a faster preparation when compared to SCPL (since it does not require a time consuming leaching step), it does require the use of solvents. Moreover, pore size is relatively small and porosity is often irregular. Freeze-drying by itself is also a commonly employed technique for the fabrication of scaffolds.

Thermally Induced Phase Separation (TIPS): Similar to emulsification/freeze-drying, TIPS requires the use of a solvent with a low melting point that is easy to sublime. For example dioxane could be used to dissolve polylactic acid, then phase separation is induced through the addition of a small quantity of water: a polymer-rich and a polymer-poor phase are formed. Following cooling below the solvent melting point and some days of vacuum-drying to sublime the solvent, a porous scaffold is obtained.

Electrospinning: A highly versatile technique that can be used to produce continuous fibers from submicrometer to nanometer diameters. In a typical electrospinning set-up, a solution is fed through a spinneret and a high voltage is applied to the tip. The buildup of electrostatic repulsion within the charged solution, causes it to eject a thin fibrous stream. A mounted collector plate or rod with an opposite or grounded charge draws in the continuous fibers, which arrive to form a highly porous network. The primary advantages of this technique are its simplicity and ease of variation. At a laboratory level, a typical electrospinning set-up only requires a high voltage power supply (up to 30 kV), a syringe, a flat tip needle and a conducting collector. By modifying variables such as the distance to collector, magnitude of applied voltage, or solution flow rate, researchers can dramatically change the overall scaffold architecture.

CAD/CAM Technologies: Because most of the above techniques are limited when it comes to the control of porosity and pore size, computer assisted design and manufacturing techniques have been introduced to tissue engineering. First, a three-dimensional structure is designed using CAD software. The porosity can be tailored using algorithms within the software. The scaffold is then realized by using ink-jet printing of polymer powders or through Fused Deposition Modeling of a polymer melt.

The mechanical properties, specific biocompatibility, and tunable biodegradability of the amino-acid derived polycarbonate-urethanes described herein make them particularly suitable for use as soft tissue fillers.

The soft tissue fillers as described herein have the advantage of being synthetic. Such materials have the advantage of improved reproducibility relative to natural biomaterials, which in turn is associated with more reliable performance and functionality. Amino-acid derived polycarbonate-urethanes based biomaterials also have the advantage of raw material availability.

In accordance with one aspect of the present invention, amino-acid derived polycarbonate-urethanes undergo biodegradation in vivo due to their chemical composition and the presence of hydrolytic esterases in the body and their biodegradation tendencies can be exploited to design specific biodegradation profiles. Suitably, monomers and other degradation byproducts can be selected such that they are not cytotoxic.

In one embodiment, the form of the soft tissue filler of the present invention is not particularly restricted. In one embodiment, the soft tissue filler is provided in the form of pellets. In one embodiment, these pellets are injectable. Suitable pellet sizes when un-hydrated are between 0.1 $mm^3$ and 100 $mm^3$, between 1 $mm^3$ and 75 $mm^3$, 50 $mm^3 \geq 25$ $mm^3$, 50 $mm^3 \geq 20$ mm3, 50 $mm^3 \geq 10$ $mm^3$ and 50 $mm^3 \geq 5$ $mm^3$. In one embodiment, the pellets are generally cylindrical pellets having a diameter of about 4 mm and a thickness of about 4 mm. These sizes are selected as showing beneficial rates of degradation and cell/tissue infiltration into the filler.

In another embodiment, there is provided a novel method for repairing soft tissue defects and, in particular, for the repair of breast defects, which comprises implanting at the site of tissue defect soft tissue filler. In one embodiment, the soft tissue filler is provided in the form of pellets, which are used to "fill" the soft tissue defect. The scaffolds may be provided in a non-hydrated form. In one embodiment, the soft tissue filler may be implanted in a non-hydrated form. In another embodiment, the soft tissue filler may be used in suspension and may be hydrated prior to use using a suitable biocompatible fluid e.g. plasma, serum, surgical exudates, saline, protein solution or gels, etc.

Unlike oncoplastic surgical techniques, amino-acid derived biodegradable polycarbonate-urethane implantation can be a simple and cost-effective procedure which does not require special equipment, extensive surgical dissection and a long surgery time (<10 min). This in turn can potentially minimize the stress on the patient's body as well as reduce the complication rates that are associated with breast surgery. Furthermore, amino-acid derived biodegradable polycarbonate-urethane fillers can avoid multi-step and costly biological processing, such as bioactive coatings, stem cell isolation, expansion and enrichment as well as autologous tissue (adipose and dermal) and PRP harvesting, which have been used in recent studies exploring partial breast reconstruction methods.

Amino-acid derived biodegradable polycarbonate-urethane may also provide a permanent solution without the need for follow up procedures. Specifically, amino-acid derived biodegradable polycarbonate-urethane supported cell/tissue growth and infiltration as well as neovascularization following its implantation in an in vivo model, and no evidence of adipose tissue resorption or breast shape/volume change was detected within the 36 week time frame. This method is unlike autologous fat transplantation which has shown adipose tissue resorption and 40-60% graft volume reduction due to insufficient neovascularization, necessitating multiple procedures to achieve a desirable outcome. While integrating well within the surrounding breast tissue, amino-acid derived biodegradable polycarbonate-urethane gradually degraded in vivo, eliciting minimal foreign body reaction and (no foreign body giant cell and fibrous capsule formation, absence of chronic inflammation and presence of angiogenesis).

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

The above description, the examples below and accompanying drawings should be taken as illustrative of the invention, and are intended to cover any variations, uses, or adaptations of the invention following, in general, the principles of the invention and including such departures from the present disclosure as come within known or customary practice within the art to which the invention pertains. The scope of the invention is therefore intended to be limited solely by the scope of the appended claims.

EXAMPLES

Example A: Preliminary Study

A.1 Materials

Anhydrous N,N-dimethylacetamide, benzoyl peroxide (BPO), dibutyltin dilaurate (DBDL), methyl methacrylate (MMA), methacrylic acid (MAA) and sodium bicarbonate (salt, 95 wt % of particles were in the range of 105-420 μm) were purchased from Sigma-Aldrich Canada and used as received. Diethyl ether (Fisher Scientific Canada) and polyethylene glycol (PEG, Polysciences Inc.) were used as received. Lysine diisocyanate (Arking Pharma, Canada) and 2-hydroxyethyl methacrylate (HEMA, Sigma-Aldrich Canada) were distilled under vacuum (0.05 mmHg) at 120° C. and 60° C., respectively to remove residual moisture, low-molecular weight impurities and partially polymerized reagents from the monomers prior to use. Poly (hexamethylene carbonate) diol (Average Mn=1006.278 g/mol, UBE America) was degassed under vacuum at 50° C. overnight prior to use.

A.2. Carbonate-Based Divinyl Oligomer Synthesis

Carbonate-based divinyl oligomer (C-DVO) was synthesized using LDI, PCN and HEMA (the respective stoichiometric molar ratio was 2.00:1.00:2.01). Degassed PCN was dissolved in anhydrous dimethylacetamide and reacted with distilled LDI in a controlled-atmosphere glove box under dry nitrogen gas. After 4 hours, distilled HEMA was added and the reaction was allowed to progress for an additional 18 hours. The reaction was conducted in the presence of DBDL catalyst (281 ppm) at a temperature of approximately 45-50° C. and was stirred continuously at 300 rpm. DVO was recovered following the precipitation of the reaction product in a diethyl ether/distilled water mixture (30/70 v/v %) and its subsequent drying under vacuum at room temperature. The synthesized C-DVO was characterized by proton nuclear magnetic spectroscopy (1H-NMR). 1H NMR (CDCl3, 298 K, 300 MHz) δ (ppm from tetramethylsilane (TMS)): 1.30-1.47 (48H, CH2-CH2-C), 1.51-1.55 (4H, CH2-CH2-NH—COO), 1.58-1.74 (44H, CH2-CH2-OCO), 1.74-1.78 (4H, CH2-CH—NH—COO), 1.93-1.97 (6H, CH3-C)CH2), 3.11-3.21 (4H, CH2-NH—COO), 3.73-3.76 (6H, CH3-OCO), 4.08-4.16 (40H, CH2-0000), 4.25-4.28 (2H, OOC—CH—NH-000), 4.28-4.40 (12H, CH2-OCO), 5.57-5.61 (2H, cis-CH2)C(CH3)COO), 6.12-6.15 (2H, trans-CH2)C(CH3)COO).

A.3 Fabrication of Porous Amino-Acid Derived Biodegradable Polycarbonate-Urethane Scaffolds Porous amino-acid derived biodegradable polycarbonate-urethane pellets (1 cm diameter, 1 cm thickness) were synthesized, by reacting the C-DVO with the MAA and MMA monomers in a final stoichiometric molar ratio of 1:5:15 (DVO:MAA:MMA). The polymerization reaction was carried out in the presence of BPO initiator (0.003 mol/mol vinyl group) at 110° C. for 24 hours. A double porogen system consisting of salt particles (95 wt % of particles are in the range of 105-420 μm) and PEG (600 Da) was used to confer macro-porosity and micro-porosity to the scaffolds respectively. The polycarbonate-urethane scaffolds were synthesized in the presence of 75 wt % porogen (10 wt % PEG, 65 wt % salt) resulting in a porous amino-acid derived biodegradable polycarbonate-urethane scaffold. Upon the completion of the curing process, the polymeric discs underwent a porogen-leaching process via soxhlet extraction for 48 hours. The resulting porous scaffolds were then dried using an ethanol gradient. Gel fraction and the extent of polymerization was determined using an analytical balance. Specifically, the weight of the amino-acid derived biodegradable polycarbonate-urethane discs were recorded (accuracy of ±0.0001 g, n=6) before and after the porogen-leaching process to determine the amount of extracted unreacted monomer.

A.4 Gamma Irradiation

Prior to implantation, dry, weighed scaffolds were gamma irradiated (2.5 Mrad 60Co, 12 h) using a Gammacell 220 (performed at Southern Ontario Centre for Atmospheric Aerosol Research (SOCAAR) Lab, University of Toronto; manufacturer: MDS Nordion).

A.5 Anesthetics and Perioperative Care

The surgical protocol was reviewed and approved by the institutional Animal Care Committee (ACC) at University Health Network. All work was performed in compliance with the standards of the Canadian Council on Animal Care (CCAC) and the Ontario Animals for Research Act.

Two female mature purpose-bred Yucatan Minipigs (retired breeders, age=4 years, weight=100-120 kg) were used in this study for a duration of nine months. The pigs were free of unknown pathogens including *Brucella suis, Mycoplasma hyopneumoniae, Leptospirosis* spp., *Actinobacillus pleuropneumoniae*, porcine circovirus 2 (PCV-2), transmissible gastroenteritis virus (TGEV), pseudorabies virus (PRV), porcine respiratory and reproductive syndrome virus (PRRSV). The pigs were housed as a group on the floor with wood shavings and rubber mats, fed a standard swine diet and ad libitum water. The pigs were handled under the care of the veterinary staff (Animal Resource Centre (ARC) of University Health Network) with regular monitoring of their attitude, activity, behavior, body weight, vital signs, blood chemistry, and wound care. This study included a total of five surgical sessions at time 0, 6, 12, 24 and 36 weeks, during which the pigs were intubated under general aneasthesia. The induction was done using a combination of intramuscular midazolam (0.3 mg/kg) and ketamine (20 mg/kg) and inhalation isoflurane. The general anesthesia was maintained with 1-3% isoflurane. Presurgical analgesia was provided with 0.01-0.05 mg/kg buprenorphine. The anesthesia was provided by the veterinary staff according to the standard practice with appropriate perioperative monitoring. At each surgical session, the pigs received prophylactic intravenous antibiotics (cefazolin 20 mg/kg). The pigs were monitored daily for 14 days and then weekly by veterinary staff for the parameters indicated above as well as the appearance of the incision. Meloxicam (0.2 mg/kg) was provided orally for two days after surgery post-operative analgesia. At week 36, the pigs were euthanized, while under deep isoflurane anesthesia for the final surgical session, by rapid bolus intravenous injection of 1-2 mEq/kg KCl.

A.6 Lumpectomy and Biomaterial Implantation Surgery

The polycarbonate-urethane scaffolds were tested as potential soft tissue fillers of breast defects post lumpectomy procedures. Prior to surgery, the pig breasts were labelled systematically according to their position on the torso and they were assigned to one of the two study groups: scaffold (A), and sham control (B; no biomaterial). Prior to the procedures, a portable ultrasound machine (Sonosite Micro-Maxx HFL38/13-6 MHz) was used to image the breasts and to document their dimensions. The skin surface was then prepped and draped with a three-stage preparation using iodine-based solutions. For each lumpectomy, a 3 cm skin incision was made using a scalpel. The incisions were oriented transversely and placed immediately inferior to the nipple-areolar complex of each breast. The lumpectomy was carried out using electrocautery to remove the normal breast tissue under the skin with a diameter of approximately 2 cm, which accounted for approximately 50% of the breast volume. Hemostasis was maintained throughout the procedures using electrocautery. The original excised breast tissue from each animal was placed in 10% buffered formalin upon retrieval and was used as histological controls. At time 0, total of eight lumpectomy sites (per animal) were loosely filled with saline-soaked amino-acid derived biodegradable polycarbonate-urethane scaffolds: four lumpectomy sites were filled with formulation A while four lumpectomy sites were with left empty (sham control). For the polycarbonate-urethane scaffolds (A) and sham control (B) per each time-point (6, 12, 24 and 36 weeks), samples were not only placed in different pigs but also different breast locations. There were two repeats per time-point for A and B. All incisions were closed using 2-0 Polysorb interrupted and 4-0 Polysorb subcuticular running sutures in the same manner as in standard lumpectomies performed in clinical cases. The incisions were then dressed with Opsite transparent occlusive dressing for easy inspection.

A.7 Mastectomy and Biomaterial Explantation Surgery

At each time-point (6, 12, 24 and 36 weeks), the pigs underwent general anesthesia and ultrasound breast examination was performed as described above. A total of 6 breasts were then excised via mastectomy: three with polycarbonate-urethane scaffold filling and three with no scaffold filling (sham control). For each mastectomy, an elliptical incision was made that included the nipple-areolar complex and the previous lumpectomy incision. The length of the mastectomy scars varied from 5-8 cm depending on the size of the breast. While keeping the seroma cavity intact within the mastectomy specimen, the entire breast was removed down to the underlying muscle fascia. The explanted tissue specimens were placed in 10% bufferred formalin immediately upon retrieval. All incisions were closed and dressed in similar manner to the lumpectomy incisions performed at time zero.

A.8 Histological Staining

At each time-point (6, 12, 24 and 36 weeks), the polycarbonate-urethane scaffold explants were subjected to histological and immunohistochemical staining. Briefly, the formalin-fixed explanted tissue specimen were subjected to paraffin embedding and sectioning. Following their dewaxing in xylene and rehydration in gradient ethanol solutions, all sections were stained with hematoxylin and eosin (H&E).

A.9 Gross Observation and Cosmetic Assessment

Pigs, implanted with polycarbonate-urethane scaffolds, did not display any abnormal behavior and healed very well with no major complications. No observable anesthetic and wound complications were detected. All the blood tests (renal and liver function tests, blood counts and electrolytes) were normal and unchanged throughout the 36 week study period. The polycarbonate-urethane scaffolds maintained breast shape up to 36 weeks post-implantation while control sites (sites with no filler) flattened. Furthermore, examination of the implant site immediately after surgery and following 36 weeks revealed that cavities filled with polycarbonate-urethane scaffolds felt stiffer to the touch than normal pig breast tissue.

A.10 Histological Analysis

Figure 14:
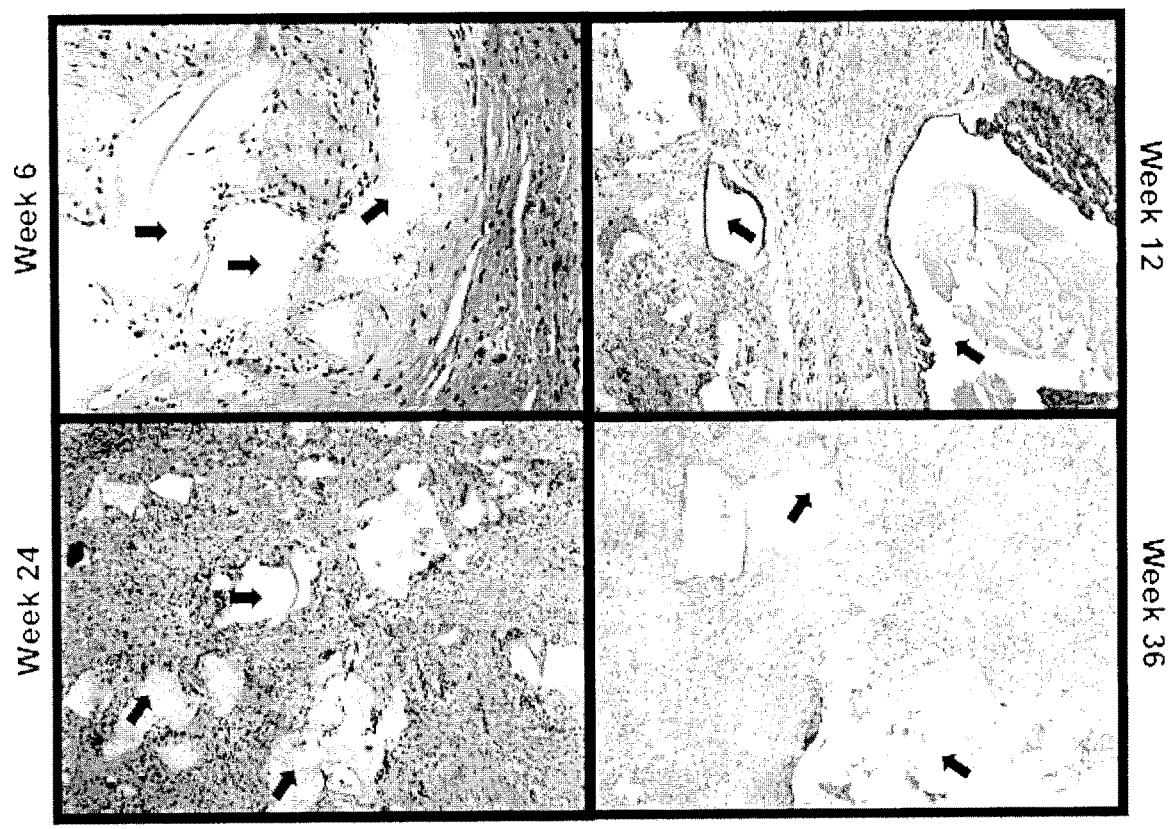
FIG. 14 shows cell and tissue distribution in explanted breast tissue following H&E histological staining. Representative histology images of breast tissue containing amino-acid derived biodegradable polycarbonate-urethane porous scaffolds of formulation C-DVO:MAA:MMA 1:5:15, in the form of 1 cm diameter by ×1 cm height (i.e. 0.8 $cm^3$ or $785^5$ $mm^3$) obtained in the presence of 75 wt % porogen after 6, 12, 24 and 36 weeks in vivo are shown. Black arrows indicate scaffold pieces. White arrows indicate new vascularization.

Histological analysis was carried out in order to evaluate cell and tissue infiltration within the amino-acid derived biodegradable polycarbonate-urethane filler resin during the implantation period (up to 36 weeks). Based on H&E (FIG. 14; stains nuclei purple, cytoplasm and extracellular matrix in pink and red blood cells in deep red)), at the early 6 week time point, cell, tissue and blood vessel (red blood cells) infiltration were observed to be more prominent at the at the edge of implant cavity when compared to the scaffold centre. At this early time-point, most cells within and around the implant cavity appear to be inflammatory cells. Furthermore, a greater presence of granulation tissue, characterized by the presence of new blood vessels and fibroblasts was observed at 6 week. At later time points (12, 24 and 36 weeks) scaffolds were observed to have integrated well within the host tissue, displaying a very thin "reactive zone" around the material where the collagen fibers were aligned. Blood vessels were present right up against the interface of the polymeric material and native tissue and an avascular fibrous capsule was not detected. Furthermore, a greater density of cell, tissue (e.g. collagen) and red blood cells was observed to infiltrate within the pores of the scaffold centre, though some areas were observed that lacked tissue infiltration H&E images were also used to assess amino-acid derived biodegradable polycarbonate-urethane degradation in vivo (FIG. 14). Signs of biomaterial fragmentation were observed and the scaffolds degraded very slowly in pigs. At the completion of study, large scaffold pieces were remaining (60-80% of the material remained) indicating a very slow degradation. Even after 36 weeks, pores were not completely infiltrated with tissue (indicated by black arrows (see FIG. 14 and compare to FIG. 15). Surgeons also assessed the implants at the completion of the study, for a qualitative assessment of stiffness (i.e. feeling for non-compliance with healthy soft tissue) The larger particulate and integrated tissue had a distinct stiffness that was a non-desirable clinical outcome since it could be confused with the presence of a tumour.

Statistical Analysis

All the other results of this work were analyzed by analysis of variance (ANOVA). For all analyses (SPSS 14.0), significance was assigned for $p<0.05$.

Example 1. Synthesis of Soft Tissue Fillers 1.1 Materials

Anhydrous N,N-dimethylacetamide, benzoyl peroxide (BPO), dibutyltin dilaurate (DBDL), methyl methacrylate (MMA), methacrylic acid (MAA) and sodium bicarbonate (salt, 95 wt % of particles are in the range of 105-420 μm) were purchased from Sigma-Aldrich Canada and used as received. Diethyl ether (Fisher Scientific Canada) and polyethylene glycol (PEG, Polysciences Inc.) were used as received. Lysine diisocyanate (Arking Pharma, Canada) and 2-hydroxyethyl methacrylate (HEMA, Sigma-Aldrich Canada) were distilled under vacuum (0.05 mmHg) at 120° C. and 60° C., respectively to remove residual moisture, low-molecular weight impurities and partially polymerized reagents from the monomers prior to use. Poly (hexamethylene carbonate) diol (Average Mn=1006.278 g/mol, UBE America) was degassed under vacuum at 50° C. overnight prior to use. Polyethylene glycol (PEG, 1000 Da, Sigma-Aldrich Canada) was degassed under vacuum at 50° C. for 48 h prior to use.

1.2. Carbonate-Based Divinyl Oligomer Synthesis

Carbonate-based divinyl oligomer (C-DVO) was synthesized using LDI, PCN and HEMA (the respective stoichiometric molar ratio was 2.00:1.00:2.01). Degassed PCN was dissolved in anhydrous dimethylacetamide and reacted with distilled LDI in a controlled-atmosphere glove box under dry nitrogen gas. After 4 hours, distilled HEMA was added and the reaction was allowed to progress for an additional 18 hours. The reaction was conducted in the presence of DBDL catalyst (281 ppm) at a temperature of approximately 45-50° C. and was stirred continuously at 300 rpm. DVO was recovered following the precipitation of the reaction product in a diethyl ether/distilled water mixture (30/70 v/v %) and its subsequent drying under vacuum at room temperature. The synthesized C-DVO was characterized by proton nuclear magnetic spectroscopy (1H-NMR).

1.3. Divinyl Oligomer Synthesis

C-DVO was synthesized using LDI, PCN, and HEMA (respective stoichiometric molar ratio of 2.00:1.00:2.01) in a controlled atmosphere glovebox under dry nitrogen gas. Briefly, degassed PCN (21.49 g) was dissolved in 175 mL of anhydrous dimethylacetamide. The reaction flask was maintained at a temperature of approximately 45-50° C. and stirred continuously at 300 rpm throughout the synthesis. Upon obtaining a homogeneous solution, distilled LDI (10.19 g) was transferred to the reaction flask. This was followed by the addition of the DBDL catalyst to yield a final optimal concentration of 281 ppm. The reaction was then allowed to progress for 4 h prior to the addition of the distilled HEMA (6.28 g). After an additional 18 h, the DVO was recovered (~97% yield) following the precipitation of the reaction product in a diethyl ether/distilled water mixture (30/70 v/v %) and its subsequent drying under vacuum at room temperature. The synthesized DVO was characterized by proton nuclear magnetic resonance spectroscopy (1H NMR). 1H NMR (CDCl3, 298 K, 300 MHz) δ (ppm from tetramethylsilane (TMS)): 1.30-1.47 (48H, CH2-CH2-C), 1.51-1.55 (4H, CH2-CH2-NH—COO), 1.58-1.74 (44H, CH2-CH2-OCO), 1.74-1.78 (4H, CH2-CH—NH-000), 1.93-1.97 (6H, CH3-C)CH2), 3.11-3.21 (4H, CH2-NH—COO), 3.73-3.76 (6H, CH3-000), 4.08-4.16 (40H, CH2-OCOO), 4.25-4.28 (2H, OOC—CH—NH—COO), 4.28-4.40 (12H, CH2-OCO), 5.57-5.61 (2H, cis-CH2)C(CH3)COO), 6.12-6.15 (2H, trans-CH2)C(CH3)COO).

Figure 2:
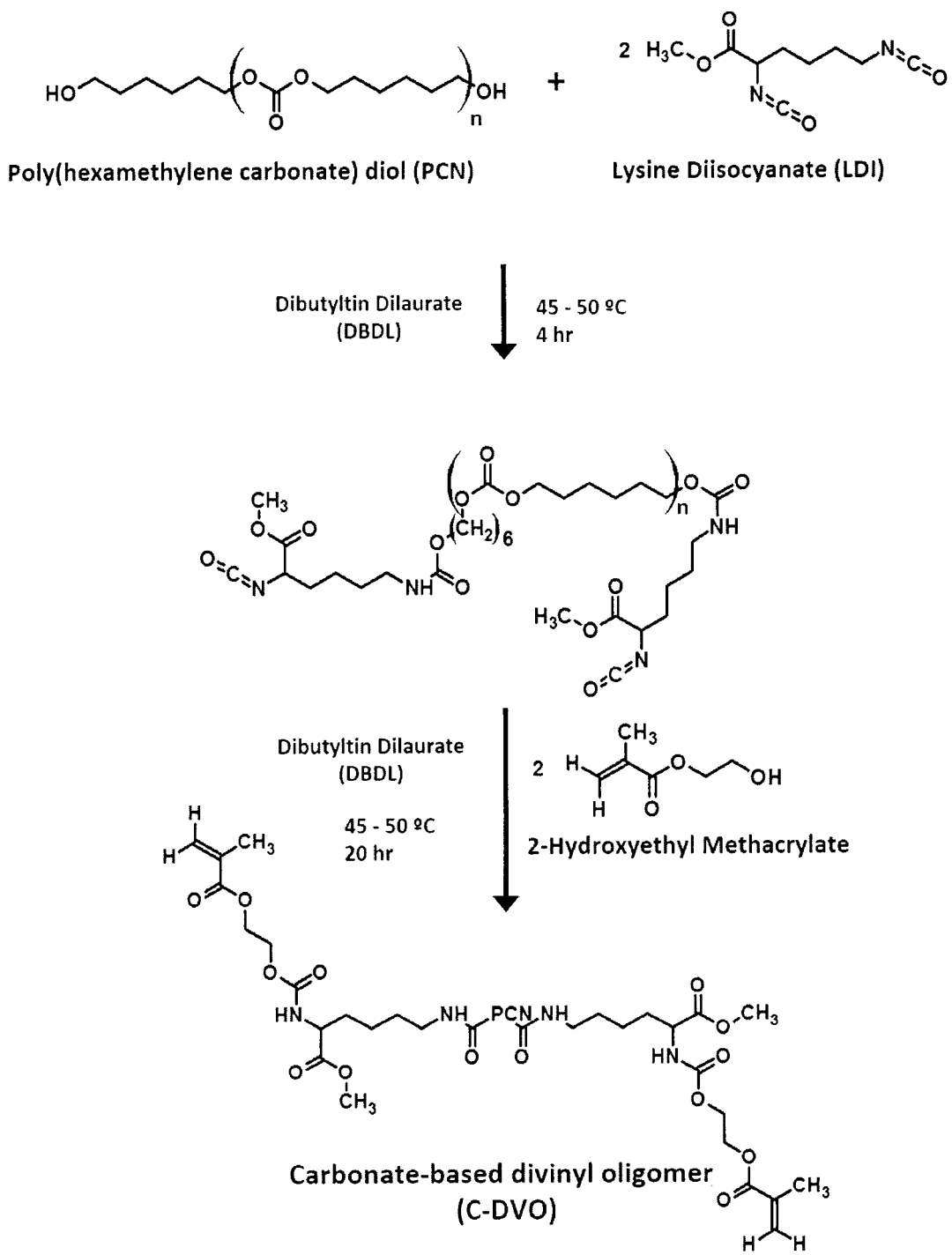
FIG. 2 shows a synthesis scheme of carbonate-based divinyl oligomer (C-DVO) in the presence of Dibutyltin Dilaurate (DBDL) catalyst.

A urethane-containing E-DVO was synthesized in the presence of DBDL catalyst and in a similar manner to C-DVO (FIG. 2) as depicted in FIG. 1. Ether-based divinyl oligomer (E-DVO) was synthesized using LDI, PEG and HEMA (respective stoichiometric molar ratio of 2.00:1.00:2.01) in a controlled-atmosphere glove box under dry nitrogen gas. Briefly, distilled LDI (10.19 g) and DBDL catalyst (0.4 mol % of total NCO groups) were dissolved in 50 mL of anhydrous dimethylacetamide. Degassed PEG (23.49 g) was dissolved in 100 mL of anhydrous dimethylacetamide and added in a dropwise manner to the stirring LDI-DBDL solution. The reaction flask was maintained at a temperature of approximately 40° C. using an oil bath and stirred continuously at 300 rpm for 1 hour, at which point, distilled HEMA (6.25 g in 25 mL of anhydrous dimethylacetamide) and DBDL catalyst (0.4 mol % of total NCO groups) were added. The oil bath was then removed from the heat source and the reaction mixture was allowed to passively cool to room temperature (~25° C.) while being continuously stirred at 300 rpm. This final stage of reaction was allowed to progress for 23 hours, resulting in a total reaction time of 24 hours. E-DVO was recovered following the precipitation of the reaction product in diethyl ether at 4° C. The synthesized E-DVO was characterized by 1H-NMR.

1.4. Divinyl Oligomer Kinetic Study

In order to monitor reaction conversion, the kinetics of E-DVO synthesis was studied. E-DVO was synthesized, according to the protocol outlined above and conversion data were collected from two reactions at specified reaction times (0.5, 1, 2, 3 and 24 hours) by withdrawing two 1 mL samples for analysis from each of the reaction flasks. The isocyanate conversion for each time point was determined by titrating the free isocyanate content in the pre-polymer reaction mixture [per David D J, Staley H B. Analytical Chemistry of the Polyurethanes: Wiley-Interscience: New York; 1969.] The collected samples were initially treated with excess 2M dibutylamine/trichlorobenzene solution overnight to react with residual isocyanates. This was then followed by the back-titration of the excess dibutylamine with 0.1N hydrochloric acid. The kinetics of C-DVO synthesis has been studied in previously published work.

Figure 3:
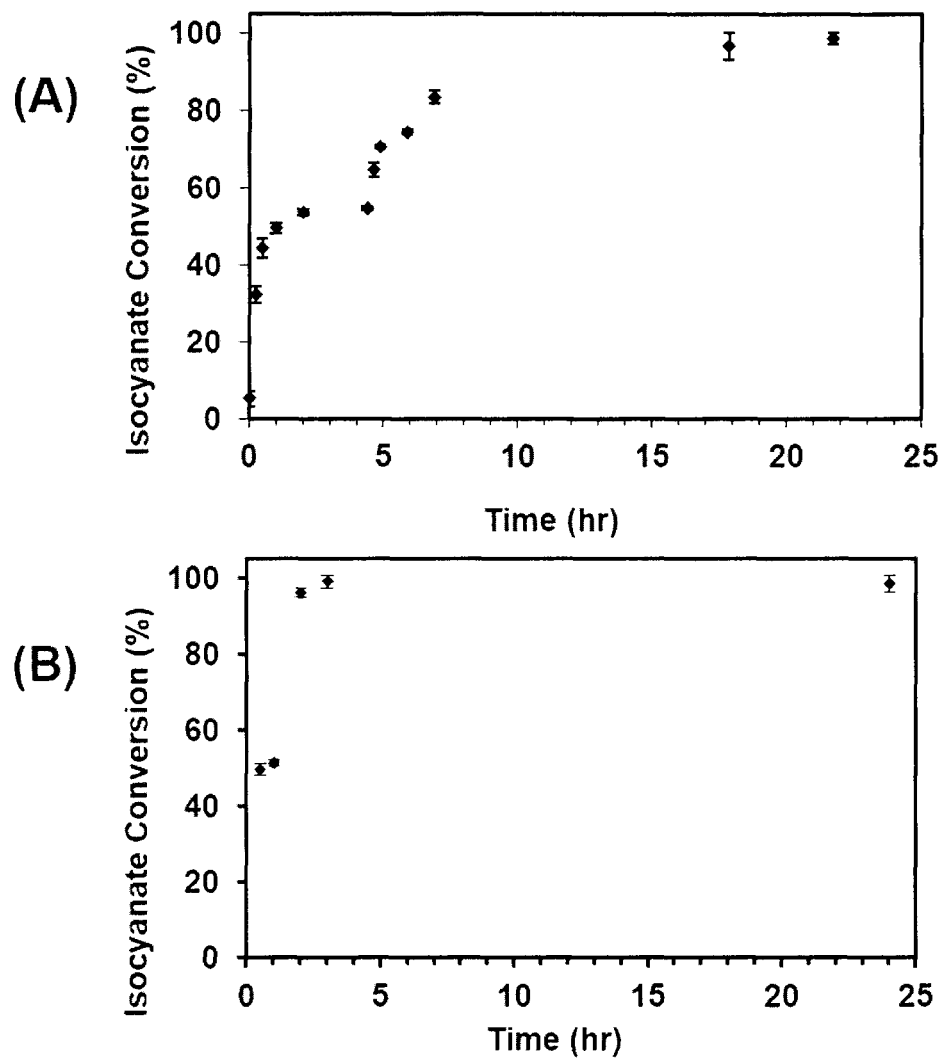
FIG. 3 shows kinetics of the (A) C-DVO synthesis and (B) E-DVO synthesis. Isocyanate conversion as a function of time is represented. (A) Lysine diisocyanate (LDI) was added to the polycarbonate (PCN) solution and reacted in the presence of DBDL for 4 hr. 2-hydroxyethyl methacrylate (HEMA) was added 4 hr after the start of the reaction. (B) Polyethylene glycol (PEG) solution was added to the LDI solution in a dropwise manner over 0.5 hr. HEMA was added 1 hour after the start of the reaction. Standard deviation bars (n=4).

The kinetic profile of isocyanate conversion during E-DVO synthesis in the presence of DBDL (0.4 mol % of total NCO groups for each step) was determined by isocyanate back-titration. As shown in FIG. 3, the first 1 hour involved the first phase of E-DVO synthesis and the reaction between LDI and PEG. The isocyanate conversion at 1 hour, was 51.3±0.8%, suggesting that 50% of the isocyanate groups had been consumed. The second phase of synthesis, which involved the LDI-HEMA reaction required an additional 2 hours for the complete conversion of the isocyanate groups (98.9±1.8% at 3 hours).

To investigate the reaction conversion of C-DVO, C-DVO was synthesized with varying concentrations of DBDL (28, 141, 281, 1030 ppm). For each concentration, two reactions were conducted and conversion data were collected at specified reaction times (0, 4, 18, and 22 h) by withdrawing two 1 mL samples for analysis from each of the reaction flasks. The isocyanate conversion for each time point was determined by titrating the free isocyanate content in the prepolymer reaction mixture. The collected samples were initially treated with excess 2 M dibutylamine/trichlorobenzene solution overnight to react with residual isocyanates. This was then followed by the back-titration of the excess dibutylamine with 0.1 N hydrochloric acid. Upon determining the optimal catalyst concentration (281 ppm), a further kinetic study with more time points was conducted to monitor isocyanate conversion over 22 h. The kinetic study demonstrated full consumption (~100%) of the isocyanate groups within 24 hours.

1.5. Fabrication of Porous Amino-Acid Derived Biodegradable Polycarbonate-Urethane Scaffolds Porous amino-acid derived biodegradable polycarbonate-urethane pellets (4 mm diameter, 4 mm thickness) were synthesized, by reacting the two DVOs with the MAA and MMA monomers in a final stoichiometric molar ratio of 1:5.5:15.5 (DVO:MAA:MMA). The polymerization reaction was carried out in the presence of BPO initiator (0.003 mol/mol vinyl group) at 110° C. for 24 hours. A double porogen system consisting of salt particles (95 wt % of particles are in the range of 105-420 μm) and PEG (600 Da) was used to confer macro-porosity and micro-porosity to the scaffolds respectively. As outlined in Table-1, amino-acid derived biodegradable polycarbonate-urethane scaffolds were synthesized in the presence of either 75 wt % porogen (10 wt % PEG, 65 wt % salt) or 80 wt % porogen (10 wt % PEG, 70 wt % PEG), resulting in a total of 8 different porous amino-acid derived biodegradable polycarbonate-urethane formulations. Upon the completion of the curing process, the polymeric pellets underwent a porogen-leaching process via soxhlet extraction for 48 hours. The resulting porous scaffolds were then dried using an ethanol gradient. Gel fraction and the extent of polymerization was determined using an analytical balance. Specifically, the weight of the amino-acid derived biodegradable polycarbonate-urethane pellets were recorded (accuracy of ±0.0001 g, n=6) before and after the porogen-leaching process to determine the amount of extracted unreacted monomer.

TABLE 1

Amino-acid derived biodegradable polycarbonate-urethane porous scaffold formulations.

| Scaffold | Porogen Content (%) | E-DVO:C-DVO (Molar Ratio) | DVO:MAA:MMA (Molar Ratio) |
|---|---|---|---|
| AAd-DPCU75-E0 | 75 | 0:100 | 1:5.5:15.5 |
| AAd-DPCU75-E10 | 75 | 10:90 | 1:5.5:15.5 |
| AAd-DPCU75-E25 | 75 | 25:75 | 1:5.5:15.5 |
| AAd-DPCU75-E50 | 75 | 50:50 | 1:5.5:15.5 |
| AAd-DPCU80-E0 | 80 | 0:100 | 1:5.5:15.5 |
| AAd-DPCU80-E10 | 80 | 10:90 | 1:5.5:15.5 |
| AAd-DPCU80-E25 | 80 | 25:75 | 1:5.5:15.5 |
| AAd-DPCU80-E50 | 80 | 50:50 | 1:5.5:15.5 |

Example 2. Characterization of Soft Tissue Fillers 2.1 Amino-Acid Derived Biodegradable Polycarbonate-Urethane Porous Scaffold Characterization In the current study, while maintaining a constant total DVO molar ratio with respect to MAA and MMA monomers (1:5.5:15.5), the C-DVO was replaced with increasing concentrations (0, 10, 25 and 50 mol %) of E-DVO in the presence of a total porogen content of 75 wt % and 80 wt %. The extent of polymerization for the resulting 8 formulations was assessed. Specifically, based on gel fraction analysis, a gel content of approximately 90% was measured for all 8 formulations demonstrating no statistically significant difference in polymerization conversion (Table 2).

TABLE 2

Gel content for porous amino-acid derived biodegradable polycarbonate-urethane scaffolds. Data are mean ± standard deviation (n = 6).

| | Gel Content (%) | |
|---|---|---|
| Scaffold Formulation | Porogen Content = 75 wt % | Porogen Content = 80 wt % |
| AAd-DPCU-E0 | 89 ± 2 | 92 ± 1 |
| AAd-DPCU-E10 | 89 ± 2 | 92 ± 1 |
| AAd-DPCU-E25 | 87 ± 2 | 92 ± 0 |
| AAd-DPCU-E50 | 89 ± 2 | 90 ± 1 |

2.2. 1H-NMR

To confirm the structure of the synthesized C-DVO and E-DVO, 1H-NMR was carried out on a Varian Mercury 400 MHz spectrometer. Samples were prepared in deuterated chloroform (30 mg/ml) and were run at room temperature. The resulting peaks were separated relative to a TMS reference.

2.3 Mechanical Testing

To assess the mechanical properties of the porous amino-acid derived biodegradable polycarbonate-urethane scaffolds, the compressive modulus was calculated.

Porous amino-acid derived biodegradable polycarbonate-urethane scaffolds were incubated in phosphate-buffered saline (PBS), supplemented with 2% penicillin-streptomycin, for 5 days at 37° C., at which point they were subjected to mechanical testing using an Instron uniaxial servo-hydraulic testing machine (Instron model 8501) equipped with a 10 N tension-compression load cell. Stress-strain data were collected for wet scaffolds (n=9) at room temperature in air at a strain rate of 1 mm/min. The compressive modulus was calculated from the data.

Figure 4:
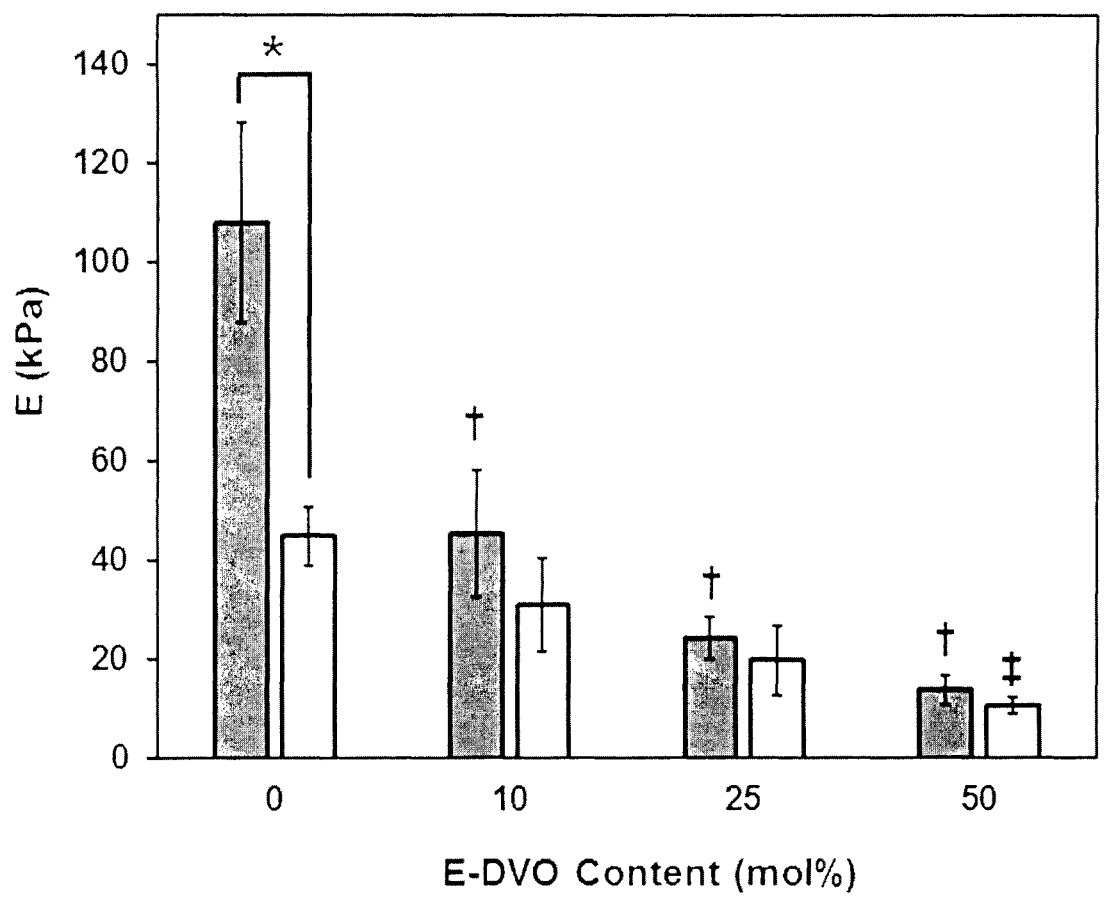
FIG. 4 shows mechanical properties of amino-acid derived biodegradable polycarbonate-urethane porous scaffolds following compression. Effect of E-DVO content on the compressive modulus of amino-acid derived biodegradable polycarbonate-urethane scaffolds prepared in the presence of 75 wt % (gray) and 80 wt % total porogen concentrations is shown. Standard deviation bars (n=9).*Statistical decrease in the presence of more porogen for scaffolds with 0 mol % E-DVO (p<0.05). †Statistical decrease with respect to scaffolds with the next lowest E-DVO concentration in the presence of 75 wt % porogen (p<0.05). ‡Statistical decrease with respect to scaffolds with the next lowest E-DVO concentration in the presence of 80 wt % porogen (p<0.05).

As shown in FIG. 4, increasing the E-DVO content (0 to 50 mol %), resulted in a gradual decrease in the compressive modulus in the presence of both 75 wt % (compressive modulus=108±20, 45±13, 24±4 and 14±3 kPa, respectively) and 80 wt % (45±6, 31±9. 20±7 and 11±2 kPa, respectively) porogen. Furthermore, for all 4 E-DVO concentrations (0, 10, 25 and 50 mol %), increasing the total porogen content from 75 to 80 wt % resulted in the decrease of the compressive modulus. However, this difference was only statistically significant for E-DVO free scaffolds.

2.4 Swelling Studies

Gravimetric analysis was used to measure polymer swelling in aqueous environments based on a previously described protocol reported by Yang et al. [Yang L, Hong J, Wang J, Pilliar R M, Santerre J P. Influence of anionic monomer content on the biodegradation and toxicity of polyvinyl-urethane carbonate-ceramic interpenetrating phase composites. Biomaterials 2005; 26(30):5951-9.] Briefly, porous amino-acid derived biodegradable polycarbonate-urethane scaffolds were incubated in PBS supplemented with 2% penicillin-streptomycin for 5 days at 37° C. Using an analytical balance, the scaffolds were weighed before and after immersion in media and their initial and final mass was recorded with an accuracy of ±0.0001 g (n=6). Prior to measuring the final scaffold weight, surface liquid was gently removed by blotting.

Figure 5:
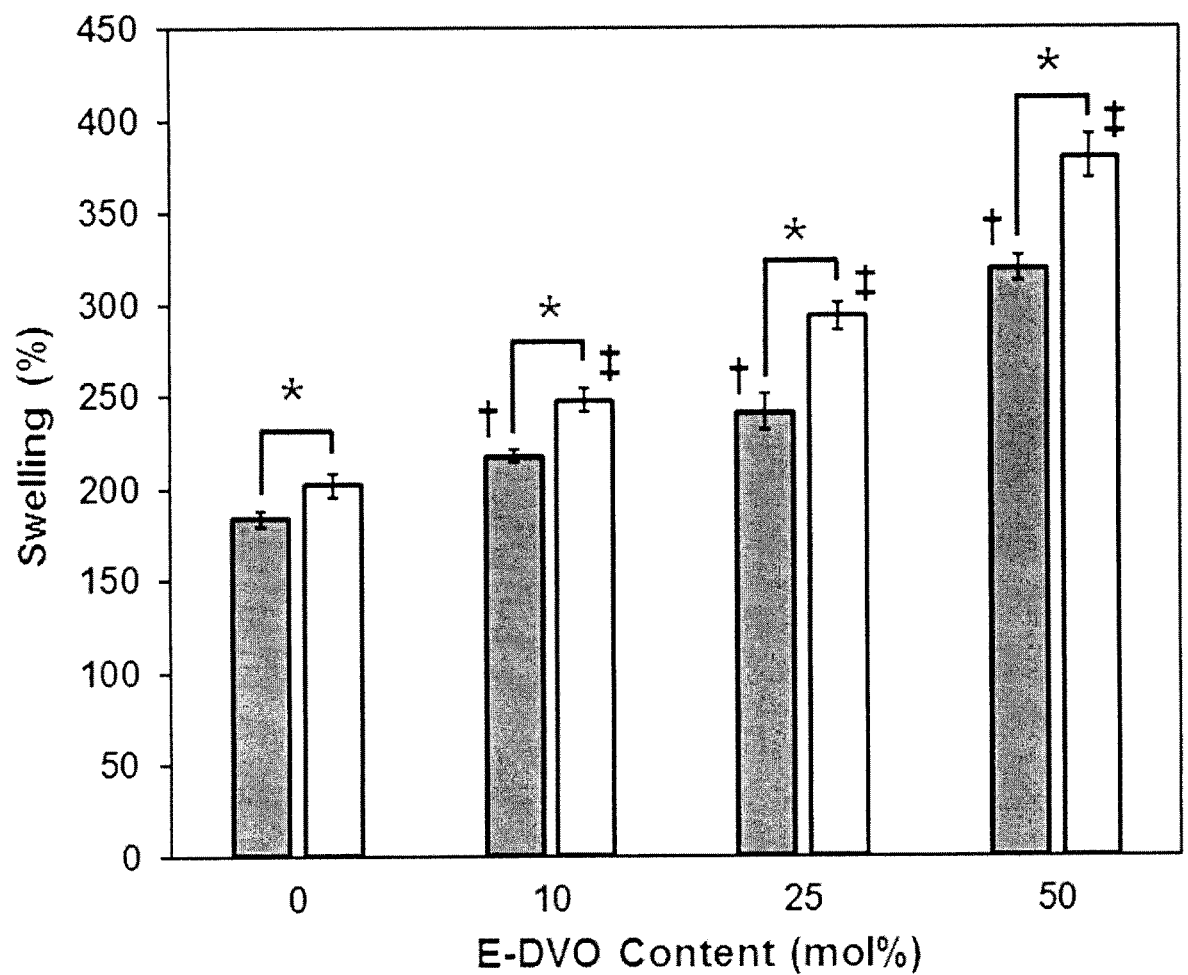
FIG. 5 shows degree of swelling of amino-acid derived biodegradable polycarbonate-urethane porous scaffolds. Effect of E-DVO content on the swelling of amino-acid derived biodegradable polycarbonate-urethane scaffolds prepared in the presence of 75 wt % (gray) and 80 wt % (white) total porogen concentration is shown. Standard deviation bars (n=6). *Statistical increase in the presence of more porogen for scaffolds with the same E-DVO content (p<0.05). †Statistical increase with respect to scaffolds with the next lowest E-DVO concentration in the presence of 75 wt % porogen (p<0.05). ‡Statistical increase with respect to scaffolds with the next lowest E-DVO concentration in the presence of 80 wt % porogen (p<0.05).

Based on gravimetric analysis the degree of amino-acid derived biodegradable polycarbonate-urethane swelling was observed to be directly related to both the E-DVO and the total porogen content (FIG. 5). Specifically, increasing E-DVO content from 0 to 50 mol % resulted in a statistical increase in amino-acid derived biodegradable polycarbonate-urethane swelling (184±4 to 320±7% for 75 wt % porogen and 202±6 to 381±12% for 80 wt % porogen). Also, for all 4 E-DVO concentrations, amino-acid derived biodegradable polycarbonate-urethane demonstrated more swelling when prepared with greater concentrations of total porogen (80 wt % versus 75 wt %).

2.5 Porosity Measurements

The degree of porosity within porous amino-acid derived biodegradable polycarbonate-urethane scaffolds was estimated by gravimetric analysis and by determining the volume of free space within each scaffold (Vvoid) with respect to the total volume of the porous scaffold (Vscaffold). To achieve this, the true density (ρpolymer) of the amino-acid derived biodegradable polycarbonate-urethane polymer was determined by measuring the mass and volume of non-porous amino-acid derived biodegradable polycarbonate-urethane pellets (6 mm diameter, 0.5 mm thickness) that were synthesized according to the protocol in Example 1 without the addition of porogens. The mass of the non-porous pellets mass was recorded using an analytical balance (accuracy of ±0.0001 g, n=9) and their volume (n=9) was estimated by measuring the height and diameter of each non-porous pellet using a digital caliper. The volume of polymeric material within the porous scaffold (Vpolymer) was then determined using the amino-acid derived biodegradable polycarbonate-urethane true density (ρpolymer) and the total porous scaffold volume (Vscaffold), which was also estimated by measuring its height and diameter using a digital caliper. Vpolymer and Vscaffold were used according to the below equation to determine total amino-acid derived biodegradable polycarbonate-urethane scaffold porosity (n=6).

$$\text{Porosity (\%)} = \frac{V_{void}}{V_{scaffold}} \times 100 = \left(1 - \frac{V_{polymer}}{V_{scaffold}}\right) \times 100$$

$$V_{polymer} = \frac{M_{scaffold}}{\rho_{polymer}}$$

Figure 6:
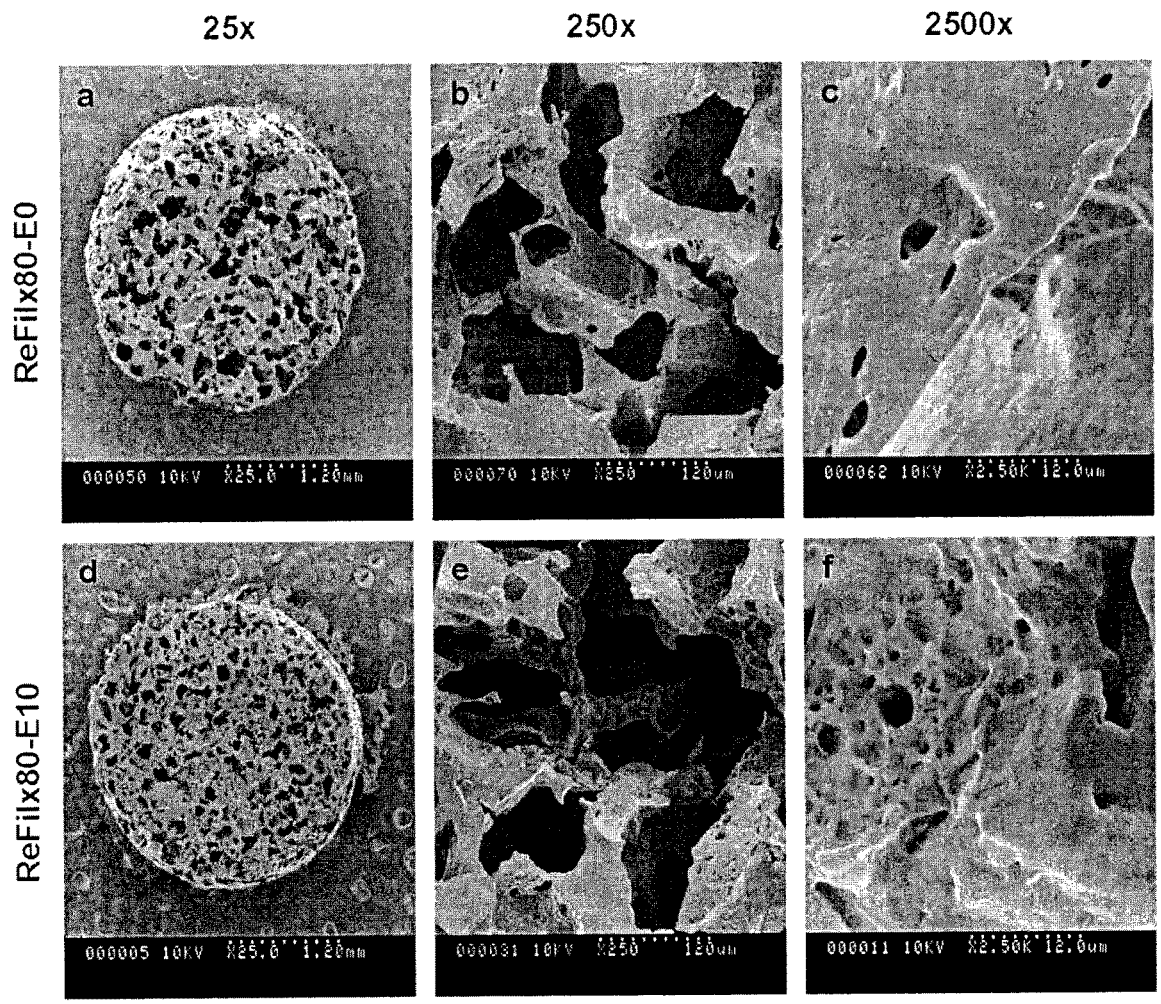
FIG. 6 shows pore morphology of the porous amino-acid derived biodegradable polycarbonate-urethane scaffolds. Scanning electron micrographs of AAd-DPCU80-E0 (formulation A, a-c) and AAd-DPCU80-E10 (formulation B, d-f) were taken at 25× (a,d), 250× (b,e) and 2500× (c,f) original magnification.

The porosity of the amino-acid derived biodegradable polycarbonate-urethane scaffolds prepared with both porogen concentrations was found to be independent of the E-DVO content and measured to be ~75-80% (Table 3). Furthermore, a slight but statistically insignificant increase in the average percent porosity for amino-acid derived biodegradable polycarbonate-urethane scaffolds prepared with 80 wt % porogen was observed when compared to those prepared with 75 wt % porogen. Based on SEM (data not shown), the cross-sectional morphology of amino-acid derived biodegradable polycarbonate-urethane scaffolds prepared with both 75 and 80 wt % porogen appeared similar and independent of the E-DVO content. Specifically, the scanning electron micrographs (FIG. 6) of the AAd-DPCU80-E0 and AAd-DPCU-E10 scaffolds, which were the selected formulations (A and B, respectively) for animal studies, did not exhibit differences in pore morphology.

TABLE 3

Percent porosity of porous amino-acid derived biodegradable polycarbonate-urethane scaffolds. Data are mean ± standard deviation (n = 6).

| Scaffold Formulation | Porosity (%) | |
|---|---|---|
| | Porogen Content = 75 wt % | Porogen Content = 80 wt % |
| AAd-DPCU-E0 | 75 ± 4 | 78 ± 1 |
| AAd-DPCU-E10 | 78 ± 2 | 81 ± 2 |
| AAd-DPCU-E25 | 77 ± 2 | 80 ± 1 |
| AAd-DPCU-E50 | 78 ± 1 | 80 ± 3 |

2.6 SEM

To investigate the surface and cross-sectional morphology, amino-acid derived biodegradable polycarbonate-urethane porous scaffolds were imaged using a Hitachi 2500 scanning electron microscope (working voltage of 10 kV) after being coated with 5 nm of platinum using SC515 SEC Coating Unit. Prior to coating, the scaffolds were dehydrated using a water/ethanol gradient.

2.7 Summary of Observation

Altering the amino-acid derived biodegradable polycarbonate-urethane polymer chemistry, by replacing C-DVO with increasing concentrations (0, 10, 25 and 50 mol %) of E-DVO, affected its physical properties. Specifically, for scaffolds fabricated with the same porogen content, increasing the E-DVO concentration decreased the compressive modulus and increased the polymer swelling. PU material properties have been known to be greatly dependent on the chemical and physical (number of hydrogen bonds between hard and soft segments) crosslinking density. However, in this work, since the total DVO content remained constant for all formulations, a difference in the total number of vinyl groups and consequently the chemical crosslinking density was not expected. This was further confirmed by the statistically similar gel content observed for all formulations. Furthermore, the replacement of the PCN soft segment with increasing concentrations of a PEG soft segment was expected to result in a direct replacement of the C═O proton acceptor groups with the C—O proton acceptor groups, suggesting no difference in the number of hydrogen bonds present between and within the hard and soft segments. As a result, the decrease in compressive modulus of the amino-acid derived biodegradable polycarbonate-urethane scaffolds fabricated with more E-DVO can be attributed to the greater concentration of the highly flexible ether linkages and the greater mobility of the PEG soft segment. Chemical crosslinking density, polymer functional groups as well as ionic moieties are important in determining polymer swelling. As indicated above, the number of vinyl groups remained the same for all amino-acid derived biodegradable polycarbonate-urethane formulations and thus, chemical crosslinking density was expected to affect the elastic-retractive forces, which oppose swelling and favor solvent expulsion, in a similar manner. Also, the replacement of the PCN soft segment with PEG, while changing the type, it does not alter the number of the proton acceptor groups (C=O versus C—O) which are capable of forming H-bonds with the surrounding water molecules. Thus, the greater degree of swelling in amino-acid derived biodegradable polycarbonate-urethane scaffolds with more E-DVO can be attributed to (1) the hydrophilic nature of the PEG component, which in turn increases the PU water absorption as well as (2) the increased mobility of the polymer chains which in turn reduces the elastic-retractive forces that oppose swelling. For the same porogen concentration, the porosity of the amino-acid derived biodegradable polycarbonate-urethane scaffolds was found to be independent of the E-DVO content and measured to be statistically similar. This suggest that despite the change in DVO composition and polymer mixture viscosity, a fairly homogeneous mixing of monomer-porogen was achieved. Furthermore, varying the amino-acid derived biodegradable polycarbonate-urethane formulation did not appear to hinder porogen leaching from the scaffolds following polymerization.

Example 3: In Vivo Study 3.1 Introduction

Based on the amino-acid derived biodegradable polycarbonate-urethane characterization studies, Formulation A (0% E-DVO) and Formulation B (10% E-DVO) were chosen to be implanted as defect fillers post lumpectomy in a porcine model. While possessing high porosity (~80%), these two formulations demonstrated mechanical properties (elastic modulus=45±6 kPa and 31±9 kPa) comparable to normal human breast tissue (elastic modulus-18-66 kPa), suggesting that a difference between the stiffness of a native breast versus a AAd-DPCU-filled breast would be difficult to detect. Both formulations also had moderate degrees of swelling (202±6% and 248±6%). While water uptake and polymer swelling are necessary to confer elasticity to AAd-DPCU scaffolds, excessive swelling can weaken the mechanical integrity of the polymeric network causing the collapse of the porous filler structure.

3.2 Gamma Irradiation

Prior to implantation, dry, weighed scaffolds were gamma irradiated (2.5 Mrad 60Co, 12 h) using a Gammacell 220 (performed at Southern Ontario Centre for Atmospheric Aerosol Research (SOCAAR) Lab, University of Toronto; manufacturer: MDS Nordion).

3.3 Anesthetics and Perioperative Care

The surgical protocol was reviewed and approved by the institutional Animal Care Committee (ACC) at University Health Network. All work was performed in compliance with the standards of the Candian Caouncil on Animal Care (CCAC) and the Ontario Animals for Research Act. Three female mature purpose-bred Yucatan Minipigs (retired breeders, age=4 years, weight=100-120 kg) were used in this study for a duration of nine months. The pigs were free of unknown pathogens including *Brucella suis, Mycoplasma hyopneumoniae, Leptospirosis* spp., *Actinobacillus pleuropneumoniae*, porcine circovirus 2 (PCV-2), transmissible gastroenteritis virus (TGEV), pseudorabies virus (PRV), porcine respiratory and reproductive syndrome virus (PRRSV). The pigs were housed as a group on the floor with wood shavings and rubber mats, fed a standard swine diet and ad libitum water. The pigs were handled under the care of the veterinary staff (Animal Resource Centre (ARC) of University Health Network) with regular monitoring of their attitude, activity, behavior, body weight, vital signs, blood chemistry, and wound care. This study included a total of five surgical sessions at time 0, 6, 12, 24 and 36 weeks, during which the pigs were intubated under general anaesthesia. The induction was done using a combination of intramuscular midazolam (0.3 mg/kg) and ketamine (20 mg/kg) and inhalation isoflurane. The general anesthesia was maintained with 1-3% isoflurane. Presurgical analgesia was provided with 0.01-0.05 mg/kg buprenorphine. The anesthesia was provided by the veterinary staff according to the standard practice with appropriate perioperative monitoring. At each surgical session, the pigs received prophylactic intravenous antibiotics (cefazolin 20 mg/kg). The pigs were monitored daily for 14 days and then weekly by veterinary staff for the parameters indicated above as well as the appearance of the incision. Meloxicam (0.2 mg/kg) was provided orally for two days after surgery post-operative analgesia. At week 36, the pigs were euthanized, while under deep isoflurane anesthesia for the final surgical session, by rapid bolus intravenous injection of 1-2 mEq/kg KCl.

3.4 Lumpectomy and Biomaterial Implantation Surgery

Two formulations of the amino-acid derived biodegradable polycarbonate-urethane family, AAd-DPCU80-E0 (formulation A) and AAd-DPCU80-E10 (formulation B) were tested as potential soft tissue fillers of breast defects post lumpectomy procedures. Prior to surgery, the pig breasts were labelled systematically according to their position on the torso and they were assigned to one of the three study groups: formulation A, formulation B and sham control (C; no biomaterial). Prior to the procedures, a portable ultrasound machine (Sonosite MicroMaxx HFL38/13-6 MHz) was used to image the breasts and to document their dimensions. The skin surface was then prepped and draped with a three-stage preparation using iodine-based solutions. For each lumpectomy, a 3 cm skin incision was made using a scalpel. The incisions were oriented transversely and placed immediately inferior to the nipple-areolar complex of each breast. The lumpectomy was carried out using electrocautery to remove the normal breast tissue under the skin with a diameter of approximately 2 cm, which accounted for approximately 50% of the breast volume. Hemostasis was maintained throughout the procedures using electrocautery. The original excised breast tissue from each animal was placed in 10% buffered formalin upon retrieval and was used as histological controls. At time 0, total of eight lumpectomy sites (per animal) were loosely filled with saline-soaked amino-acid derived biodegradable polycarbonate-urethane scaffolds: four lumpectomy sites were filled with formulation A while four lumpectomy sites were filled with formulation B. An additional four lumpectomy sites (per animal) were left empty (sham control). For every AAd-DPCU formulation (A and B) and sham control (C) per each time-point (6, 12, 24 and 36 weeks), samples were not only placed in different pigs but also different breast locations.

There were three repeats per time-point for every formulation. All incisions were closed using 2-0 Polysorb interrupted and 4-0 Polysorb subcuticular running sutures in the same manner as in standard lumpectomies performed in clinical cases. The incisions were then dressed with Opsite transparent occlusive dressing for easy inspection.

3.5 Mastectomy and Biomaterial Explantation Surgery

At each time-point (6, 12, 24 and 36 weeks), the pigs underwent general anesthesia and ultrasound breast examination was performed as described above. A total of nine breasts were then excised via mastectomy: three with formulation A filling, three with formulation B filling and three with no AAd-DPCU filling (sham control). For each mastectomy, an elliptical incision was made that included the nipple-areolar complex and the previous lumpectomy incision. The length of the mastectomy scars varied from 5-8 cm depending on the size of the breast. While keeping the seroma cavity intact within the mastectomy specimen, the entire breast was removed down to the underlying muscle fascia. The explanted tissue specimens were placed in 10% bufferred formalin immediately upon retrieval. All incisions were closed and dressed in similar manner to the lumpectomy incisions performed at time zero.

3.6 Histological Staining

At each time-point (6, 12, 24 and 36 weeks), the AAd-DPCU explants were subjected to histological and immunohistochemical staining. Briefly, the formalin-fixed explanted tissue specimen were subjected to paraffin embedding and sectioning. Following their dewaxing in xylene and rehydration in gradient ethanol solutions, all sections were stained with hematoxylin and eosin (H&E) as well as Masson's trichrome staining. De-paraffinized and rehydrated AAd-DPCU sections were also subjected to CD31 immunohistochemical staining. Antigen retrieval or unmasking was achieved via Heat Induced Epitope Retrieval (HIER), which involved the microwaving of the tissue sections in Tris-EDTA buffer (pH 9.0) solution. Endogenous peroxidase activity was blocked using 3% hydrogen peroxide. Following incubation (20 min) in normal horse blocking serum (2.5%), the sections were treated with anti-CD31 rabbit polyclonal antibody (Santa Cruz Biotechnology, sc-1506, diluted 1:2000) for 1 hour. Color development and positive staining was achieved using the ImmPRESS™ HRP Anti-Rabbit IgG (Peroxidase) polymer detection kit (Vector Labs, MP-7401) followed by treatment with freshly prepared diaminobenzidine (DAB) peroxidase substrate (DAKO, K3468). Finally, sections were counterstained lightly with Mayer's Hematoxylin, dehydrated and mounted with Permount mounting medium (Fisher Scientific, SP15-500). For all types of histological stains and each time-point, staining was conducted on two cross-sectional slices for every explant sample (6 slices per formulation). Three different regions of each cross-sectional slice were imaged (20× objective) by two different research associates (3 images/slice/associate). The faint staining of the amino-acid derived biodegradable polycarbonate-urethane PU scaffolds post exposure to histological stains aided in highlighting the scaffold within in the explanted tissue. As a result, images obtained from H&E-stained samples were used to obtain a semi-quantitative measure of amino-acid derived biodegradable polycarbonate-urethane degradation post-implantation. Briefly, Image-Pro Premier was used to measure the surface area of the scaffold fragments present in each image in order to obtain the size distribution of scaffold fragments for each formulation at different periods of implantation. Furthermore, to obtain a semi-quantitative measure of angiogenesis, the number of CD31-positive structures within each anti-CD31-stained image was also obtained using Image J (Counter Plugin).

3.7 Gross Observation and Cosmetic Assessment

Figure 7:
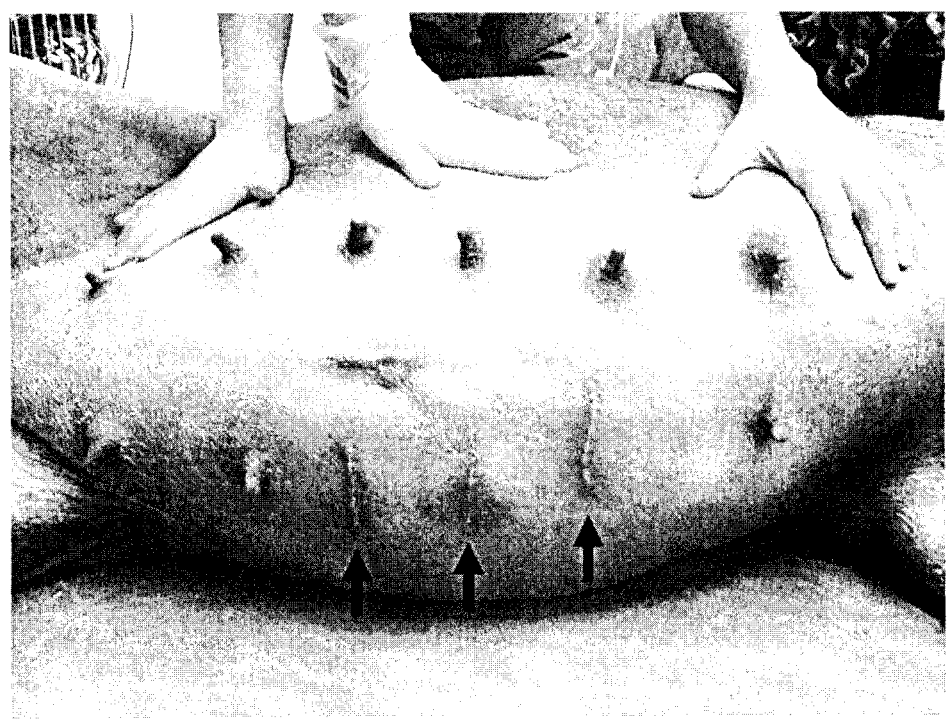
FIG. 7 shows surgery and implant site. A representative image of a pig torso at 6 weeks immediately following the first set of mastectomies is shown. Black arrows: mastectomy sites.

Pigs, implanted with both AAd-DPCU formulations, did not display any abnormal behavior and healed very well with no major complications. No observable anesthetic and wound complications were detected except for one minor wound infection (local redness only) in one of the 36 breast incisions which was treated with oral antibiotics for 1 week (amoxicillin/clavulanic acid 11-13 mg/kg daily). All the blood tests (renal and liver function tests, blood counts and electrolytes) were normal and unchanged throughout the 36 week study period. Both AAd-DPCU formulations maintained breast shape up to 36 weeks post-implantation while control sites (sites with no filler) flattened. Furthermore, examination of the implant site immediately after surgery and following 36 weeks revealed that AAd-DPCU-filled cavities felt natural to the touch and there no noticeable difference in stiffness between the AAd-DPCU-filled and control cavities. Refer to FIG. 7.

3.8 Histological Analysis

Figure 8:
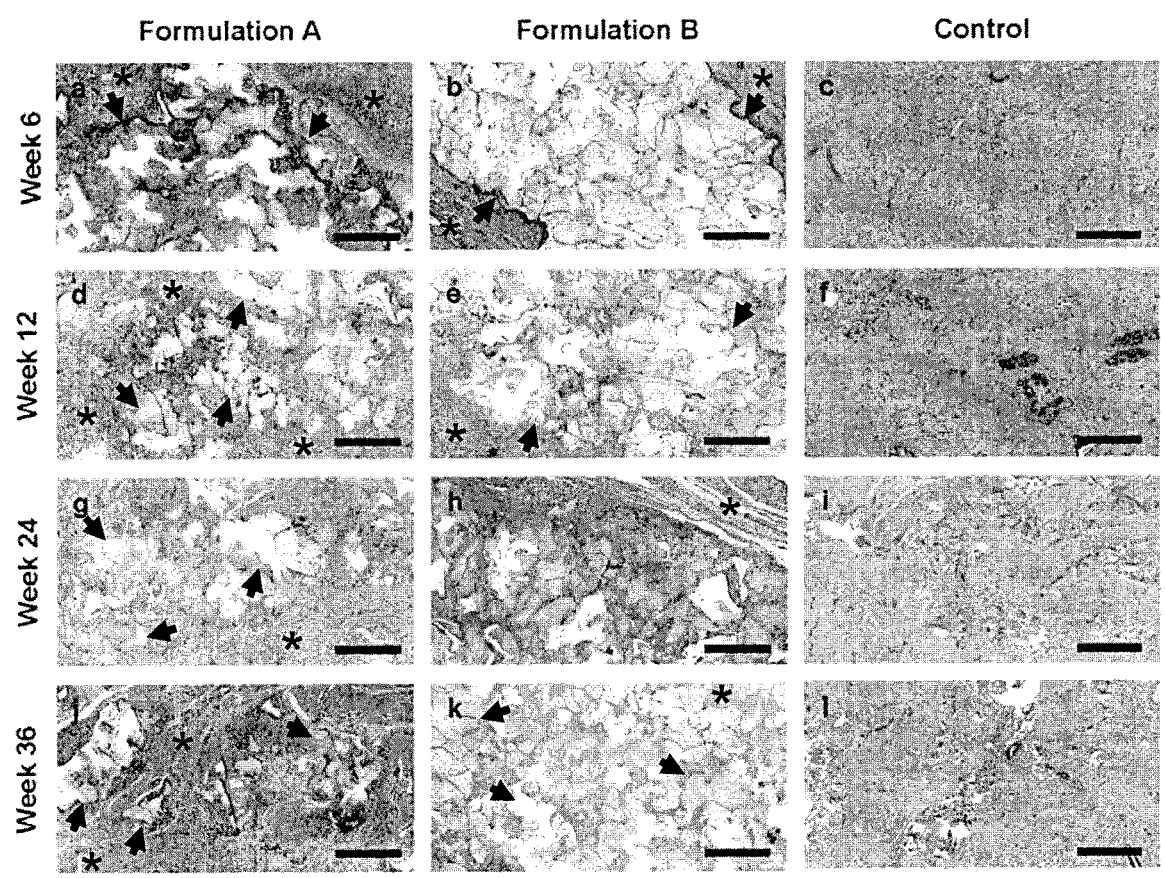
FIG. 8 shows cell and tissue distribution in explanted breast tissue following H&E histological staining. Representative histology images of breast tissue containing formulation A (a,d,g,j), formulation B (b,e,h,k) or no amino-acid derived biodegradable polycarbonate-urethane (control; c,f,i,l) after 6 (a-c), 12 (d-f), 24 (g-i) and 36 (j-l) weeks in vivo are shown. Arrows indicate scaffold pieces. Asterisks indicate areas high in cells and extracellular matrix. Scale bars represent 500 μm.
Figure 9:
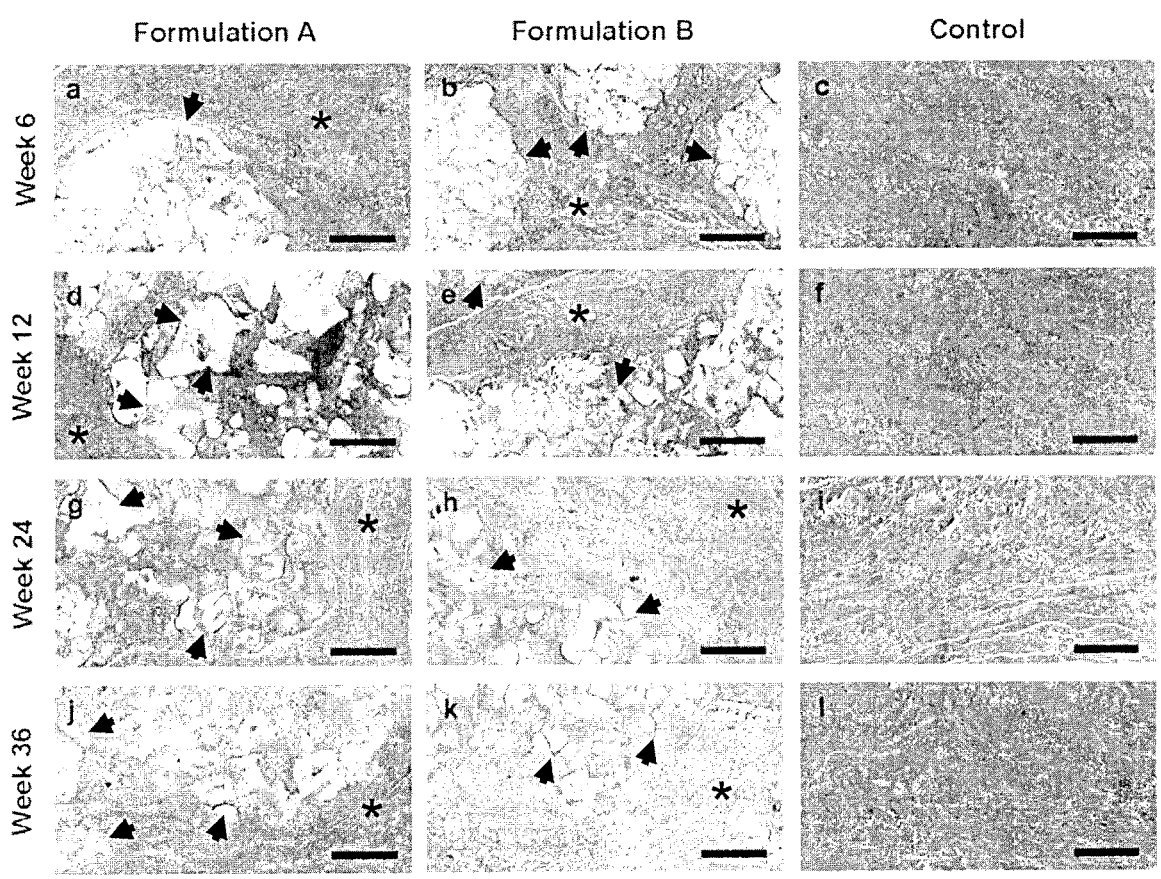
FIG. 9 shows cell and tissue distribution in explanted breast tissue following Masson's trichrome histological staining. Representative histology images containing formulation A (a,d,g,j), formulation B (b,e,h,k) or no amino-acid derived biodegradable polycarbonate-urethane (control; c,f, i,l) after 6 (a-c), 12 (d-f), 24 (g-i) and 36 (j-l) weeks in vivo are shown. Arrows indicate scaffold pieces. Asterisks indicate areas high in cells and extracellular matrix. Scale bars represent 500 μm.

Histological analysis was carried out in order to evaluate cell and tissue infiltration within the amino-acid derived biodegradable polycarbonate-urethane filler resin during the implantation period (up to 36 weeks). Based on H&E (FIG. 8; stains nuclei purple, cytoplasm and extracellular matrix in pink and red blood cells in deep red) and Masson's trichrome staining (FIG. 9; stains nuclei black and collagen blue), at the early 6 week time point (FIGS. 8 and 9, image a-b), cell, tissue and blood vessel (red blood cells) infiltration were observed to be more prominent at the at the edge of implant cavity when compared to the scaffold centre, for both AAd-DPCU formulations. At this early time-point, most cells within and around the implant cavity appear to be inflammatory cells. Furthermore, a greater presence of granulation tissue, characterized by the presence of new blood vessels and fibroblasts was observed at 6 and. At later time points (12, 24 and 36 weeks, FIGS. 8 and 9, image d-e, g-h and j-k), both AAd-DPCU scaffolds were observed to have integrated well within the host tissue, displaying a very thin "reactive zone" around the material where the collagen fibers were aligned. Blood vessels were present right up against the interface of the polymeric material and native tissue and an avascular fibrous capsule was not detected. Furthermore, a greater density of cell, tissue (e.g. collagen) and red blood cells was observed to infiltrate within the pores of the scaffold centre for both AAd-DPCU formulations. No foreign body giant cells were detected throughout the implantation period.

Figure 10:
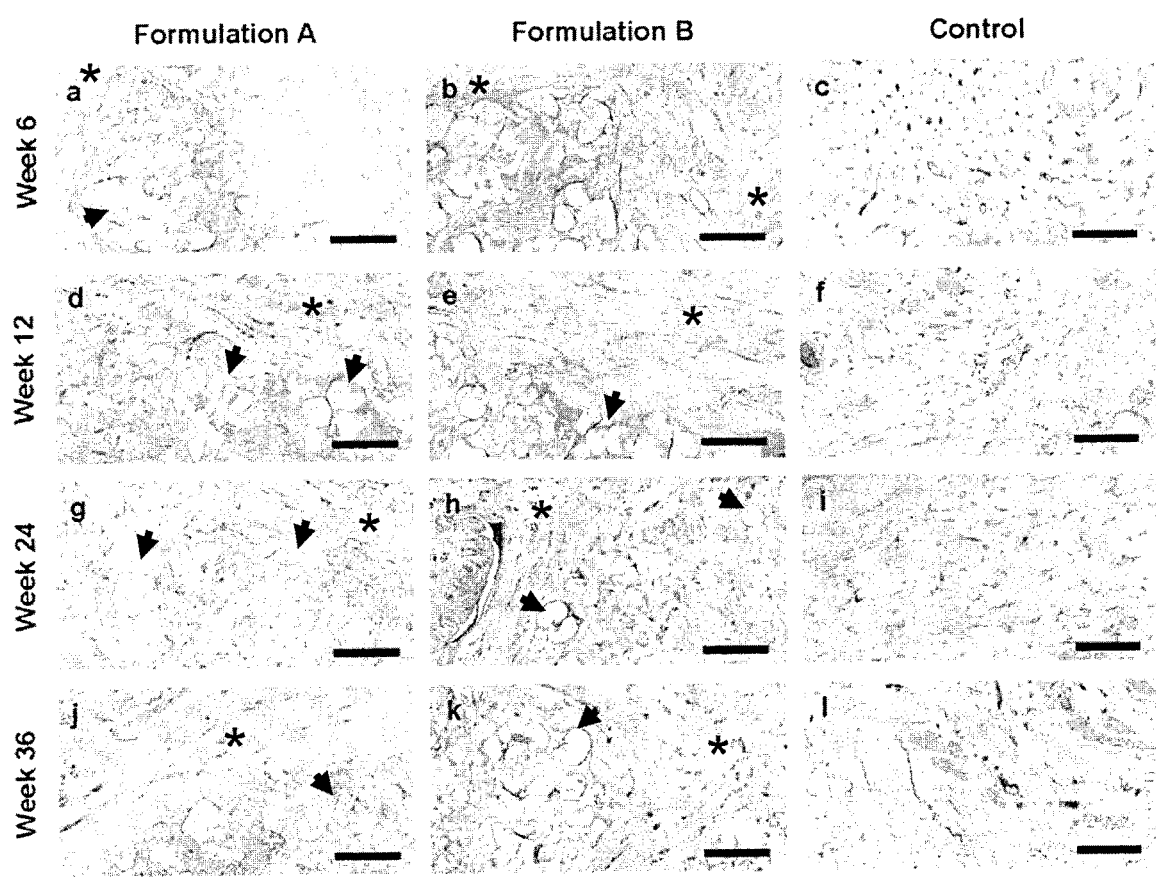
FIG. 10 angiogenesis and CD31 expression in explanted breast tissue. Representative immunohistochemistry images containing formulation A (a,d,g,j), formulation B (b,e,h,k) or no amino-acid derived biodegradable polycarbonate-urethane (control; c,f,i,l) after 6 (a-c), 12 (d-f), 24 (g-i) and 36 (j-l) weeks in vivo are shown. Arrows indicate scaffold pieces. Asterisks indicate areas high in cells and extracellular matrix. Dark punctate spots indicate positive staining for CD31. Scale bars represent 500 μm.
Figure 11:
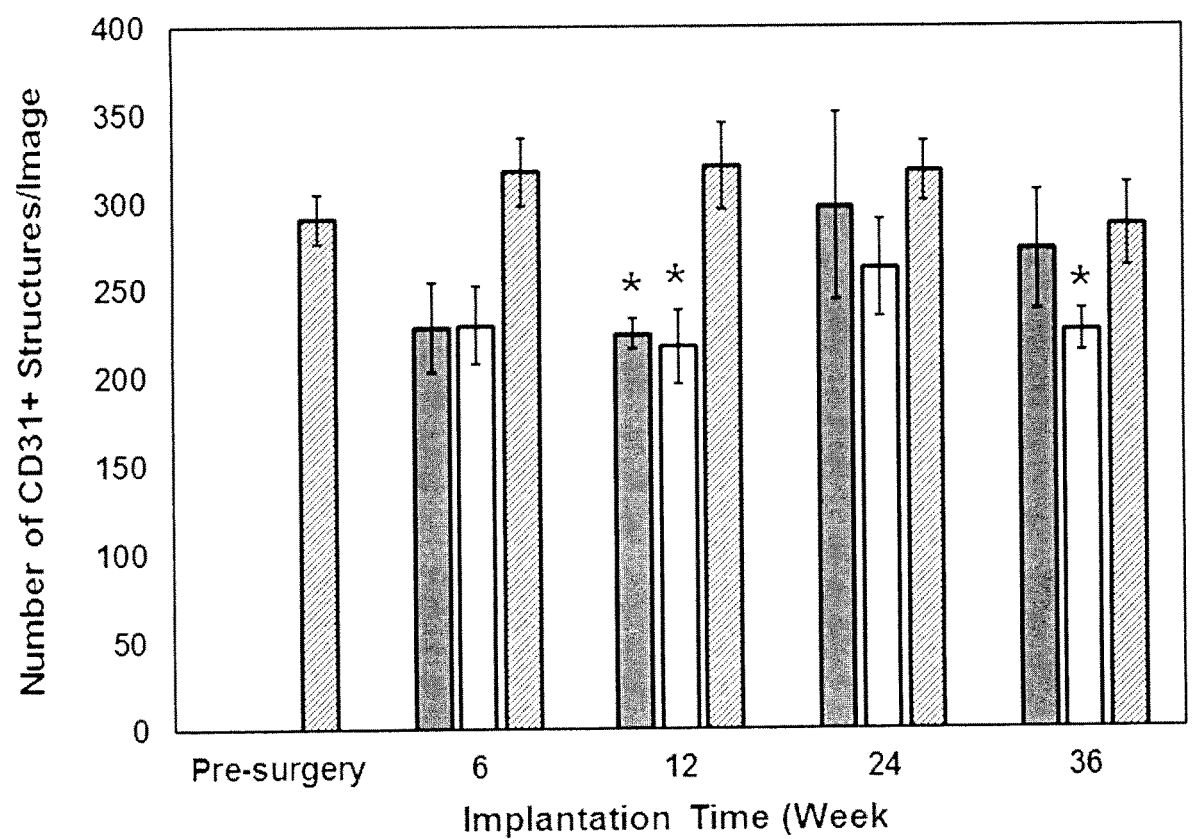
FIG. 11 shows quantification of CD31 expression in vivo. The number of CD31-positively stained structures in explanted breast tissue containing formulation A (gray), formulation B (white) or no amino-acid derived biodegradable polycarbonate-urethane (control, hashed) was determined per image at different time-points. Standard error bars (n=4-6). *Statistical decrease with respect to the native breast tissue pre-surgery control (p<0.05).

To assess blood vessel formation, the expression of CD31, a marker of angiogenesis, was studied using immunohistochemical staining. As observed in H&E and Masson's trichrome histological analysis, at the earlier time-points (6 and 12 weeks, FIG. 10, image a-b and d-e), CD31 expression was very limited within the scaffold core and mainly observed at the edge of the implant cavity. However, the amino-acid derived biodegradable polycarbonate-urethane explants following 24 and 36 weeks showed an increased expression of CD31 in all areas of the implant (FIG. 10, image g-h and j-k). Quantification of CD31+ structures using Image J confirmed the latter results (FIG. 11). Specifically, AAd-DPCU-filled cavities showed a lower number of CD31+ structures when compared to the native tissue. However, at 24 weeks, more CD31+ structures were present at levels statistically comparable to the native tissue. These levels were maintained at 36 weeks. The number of CD31+ structures in the control explants, which were obtained from AAd-DPCU-free mastectomy sites, were statistically similar to that of native tissue (pre-surgery).

Figure 12:
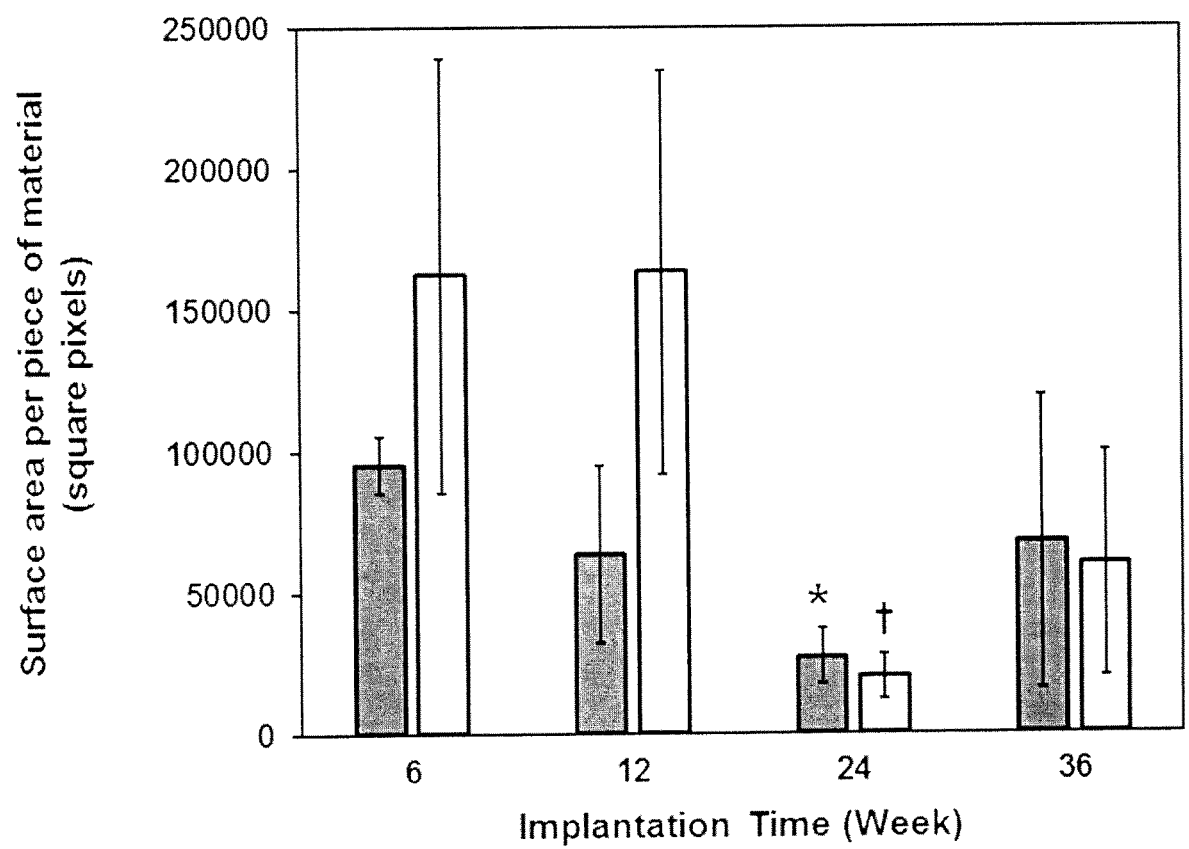
FIG. 12 shows porous amino-acid derived biodegradable polycarbonate-urethane scaffold degradation in vivo. The average size of scaffold fragments remaining at different time-points post-implantation was quantified for both formulation A (AAd-DPCU80-E0, gray) and formulation B (AAd-DPCU80-E10, white). Standard error bars (n=5-6). *Statistical decrease at 24 weeks when compared to 6 weeks for formulation A (p<0.05). †Statistical decrease at 24 weeks when compared to 6 weeks for formulation B (p<0.05).

H&E images were also used to assess amino-acid derived biodegradable polycarbonate-urethane degradation in vivo. Specifically, the average size of the scaffold fragments at different implantation periods was determined. As shown in FIG. 12, the size of the scaffold fragments generally decreased with implantation time, indicating scaffold degradation and breakdown in vivo. A slight but statistically insignificant increased in scaffold fragment size was observed at 36 weeks, which may be attributed to the full resorption of the smaller scaffold pieces while larger fragments still remained.

3.9 Ultrasound Imaging

Figure 13:
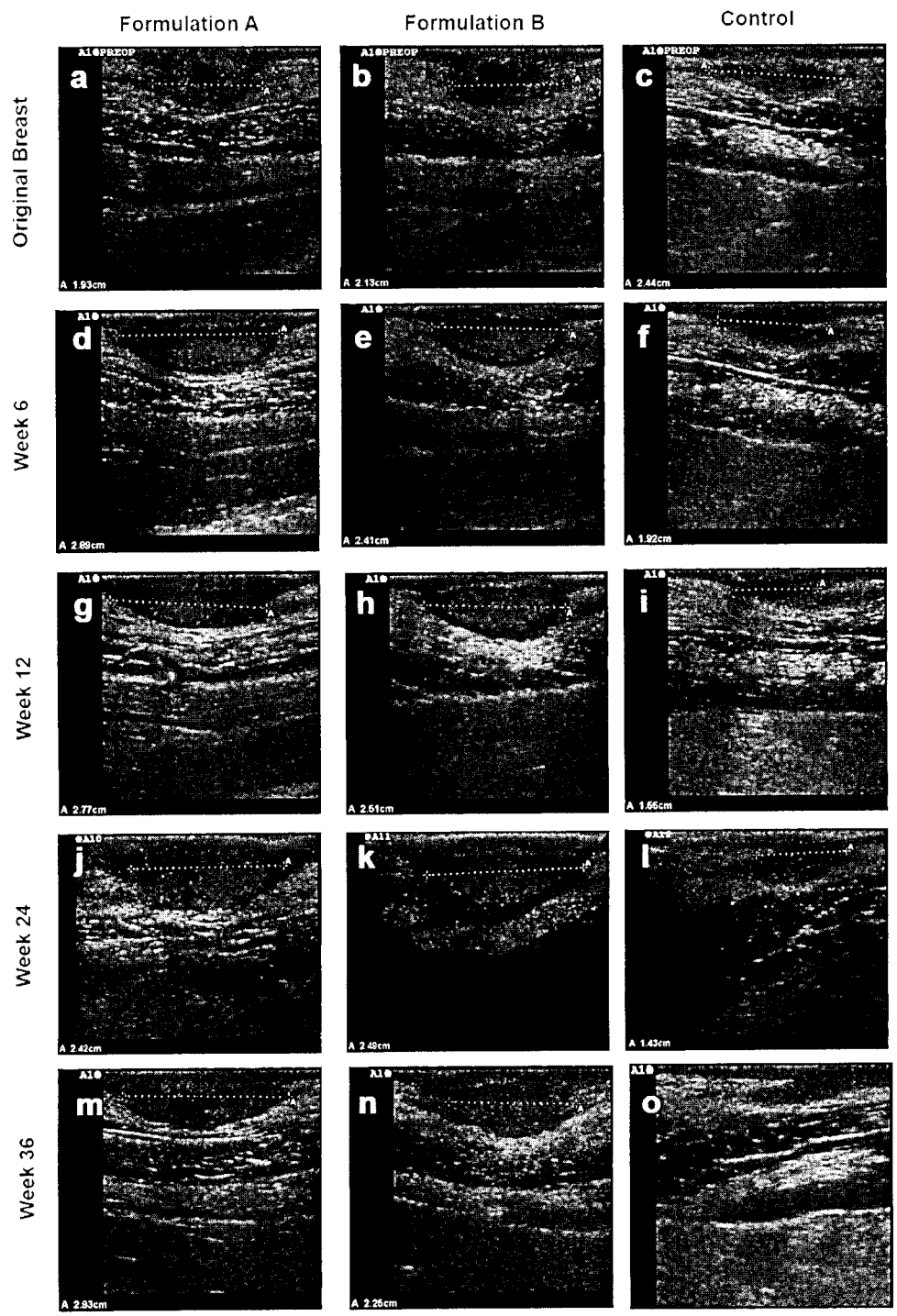
FIG. 13 shows ultrasound examination of porcine breast. Representative ultrasound images of the original porcine breast, prior to lumpectomy and amino-acid derived biodegradable polycarbonate-urethane filling are shown (a-c). Representative images of the breasts following lumpectomy and subsequent filling with amino-acid derived biodegradable polycarbonate-urethane (formulation A (d,g,j,m) or formulation B (e,h,k,n) or no amino-acid derived biodegradable polycarbonate-urethane filling (control; f,i,l,o) at 6 (d-f), 12 (g-i), 24 (j-l) and 36 weeks (m-o) are depicted.

Prior to the procedures, a portable ultrasound machine (Sonosite MicroMazz HFL38/13-6 MHz) was used to image the breasts and document their dimensions. The diameter of the original breast tissue, prior to lumpectomy and amino-acid derived biodegradable polycarbonate-urethane implantation, as measured by ultrasound, varied depending on their locations on the torso. Specifically, the average diameter was 2.54 cm (range: 1.38-3.47 cm). Representative images are shown in FIG. 13 (a-c). Representative ultrasound images of one of the three pigs over the 36 week study period are also illustrated (FIG. 13). At week 6, 12, 24 and 36, the lumpectomy cavities implanted with formulation A and B retained their volumes. However, the control breasts, in the absence of AAd-DPCU, initially demonstrated a collection of fluid/dense tissue build-up and then completely flattened and resolved by 36 weeks. A noticeable difference in the performance of the two AAd-DPCU formulations was not observed.

3.10 Summary of Observation

Histological analysis (H&E and Masson's trichrome) revealed an increase in cell and tissue presence within the centre of the implant cavity over time and by 36 weeks, amino-acid derived biodegradable polycarbonate-urethane was observed to have become fully integrated within the host tissue. This suggests that despite the absence of bioactive agents and coatings, the amino-acid derived biodegradable polycarbonate-urethane PU chemistry renders it conductive to host tissue regeneration, supporting the attachment, viability and infiltration of various cell types. In addition to their favorable chemistry, the amino-acid derived biodegradable polycarbonate-urethane fillers' high porosity and pore-interconnectivity may also play an important role in the enhanced cell and tissue distribution observed in this work. Scaffolds with high porosity and pore-interconnectivity that allow for greater mass transport (nutrient and waste diffusion) may demonstrate improved cell/tissue infiltration throughout the 3-dimensional network. This property also has been observed to play a significant role in ensuring scaffold integration within the host tissue following implantation.

Histological assessment also demonstrated a decrease in the density of inflammatory cells within and around the implant cavity with time, the absence of foreign body giant cells, the presence of blood vessels at the polymer-host tissue interface as well as within the polymeric network and the absence of an avascular fibrous capsule which is typically observed with implanted biomaterials such as polylactic-glycolic acid (PLGA). These observations suggests that both amino-acid derived biodegradable polycarbonate-urethane filler formulations, while integrating well within the host tissue, support wound repair and do not elicit chronic inflammation and infection in vivo.

Immunohistochemical analysis further confirmed the ability of both amino-acid derived biodegradable polycarbonate-urethane formulations to support neovessel formation by the observed increase of CD31 expression at the edge and centre of the implant cavity over the first 24 weeks of implantation to levels statistically comparable to the native breast tissue (FIGS. 10 and 11). These levels were maintained at 36 weeks. CD31 (platelet endothelial cell adhesion molecule-1), a type I transmembrane glycoprotein, is highly expressed on endothelial cells and at various levels on monocytes, granulocytes and platelets. It has been shown to play an important role in angiogenesis and several studies have correlated CD31 expression with neovascularization. AAd-DPCU's ability to support vascularization is important to ensure the sufficient supply of nutrients to and the survival of the regenerated tissue. The human breast is mainly composed of mature adipose tissue, which has been shown to have a high degree of vascularity. Ongoing angiogenesis is essential to the sustenance of adipose tissue growth and differentiation of preadipocytes.

The faint staining of the amino-acid derived biodegradable polycarbonate-urethane PU post exposure to the histology dyes aided in identifying the filler fragments within the explanted tissue and in assessing amino-acid derived biodegradable polycarbonate-urethane degradation in vivo. D-PHI PUs have exhibited staining following their exposure to not only histological dyes but also several fluorescent dyes. It should be noted that the faint staining of the amino-acid derived biodegradable polycarbonate-urethane filler also provided an enhanced frame of reference, aiding in highlighting the position, extent of infiltration and general distribution of cells, tissue and blood vessels within the filler porous structure. The assessment of the histological images demonstrated a decrease in the average polymer fragment size with respect to implantation time up to 24 weeks, suggesting amino-acid derived biodegradable polycarbonate-urethane PU degradation and breakdown in vivo.

The exception to this trend was at 36 weeks, where a slight increase in amino-acid derived biodegradable polycarbonate-urethane fragment size was observed. This may be attributed to the full resorption of the smaller polymer pieces, resulting in the presence of a greater density of larger fragments. Since both hydrolytic and oxidative mechanisms of degradation are present in an in vivo setting, they may both simultaneously contribute to biomaterial breakdown. Specifically, the presence of polycarbonate (C-DVO) and polyether (E-DVO) soft segments within the amino-acid derived biodegradable polycarbonate-urethane chemistry, render the polymer susceptible to both hydrolytic and oxidative degradation, respectively. The hydrophilic PEG (E-DVO) within the PU soft segment may further contribute to amino-acid derived biodegradable polycarbonate-urethane breakdown, by increasing water absorption and accelerating the degradation of the polymer's hydrolysable linkages. Furthermore, the high porosity and pore-interconnectivity of amino-acid derived biodegradable polycarbonate-urethane will lead to the availability of more surface contact area for polymer hydrolysis, which in turn may contribute to polymer degradation.

Figure 15:
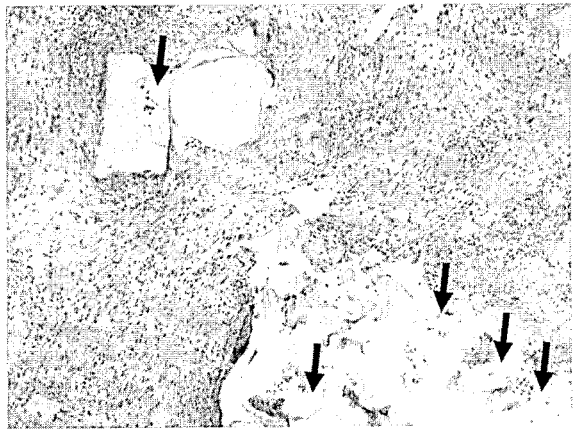
FIG. 15 shows a comparison of histological staining (H&E) images comparing two scaffolds where one A) is made from a polycarbonate DVO of the nature described in this submission, MAA and MMA in a ratio of 1:5:15 respectively, with a porosity of 75%, with size of 785 $mm^3$; and B) is made of the same 3 monomers but in a ratio of 1:5.5:15.5, with a porosity of 80%, with a size of approx. 50 $mm^3$. The images compared H&E stained histology sections for porcine breast explants at 36 weeks. Black arrows indicate empty pores. White arrows indicate scaffold pieces surrounded by tissue.
Figure 15:

FIG. 15 shows a comparison of histological staining (H&E) images comparing two scaffolds. A) is made from a polycarbonate DVO of the nature described in this submission, MAA and MMA in a ratio of 1:5:15 respectively, with a porosity of 75%, with size of 785 mm$^3$, which is a scaffold of the type prepared and used in the Preliminary Study (Example A). B) is made of the same 3 monomers but in a ratio of 1:5.5:15.5, with a porosity of 80%, with a size of approx. 50 mm³. The images compared H&E stained histology sections for porcine breast explants at 36 weeks. Black arrows indicate pores that have not yet been infiltrated with tissue. White arrows indicate scaffold material surrounded by new tissue. One can note that A) still has very large material fragments with pores in the fragments still visible and poor tissue infiltration in the pores whereas B) has only small particulate (no noticible fragments with pores) remaining (most of the material is degraded) with extensive tissue occupying the embodiment. This example highlights the importance of the correct monomer ratio, porosity and size of scaffold for achieving a timely degradation and generation of integrated tissue/implant material where there is mechanical compliance between the host tissue and the residual integrated scaffold/tissue replacement.

Example 4. Effect of the Ratio of DVO:Methacrylate on Mechanical Properties and Swelling 4.1 C-DVO Synthesis C-DVO was synthesized as outlined in Example 1.1-1.3.

4.2 Fabrication of Porous Amino-Acid Derived Biodegradable Polycarbonate-Urethane Scaffolds with Varying DVO:Methacrylate Ratios Porous amino-acid derived biodegradable polycarbonate-urethane pellets (4 mm diameter, 4 mm thickness) were synthesized, by reacting C-DVO with the MAA and MMA monomers the stoichiometric ratios outlined in Table 4. The polymerization reaction was carried out in the presence of BPO initiator (0.003 mol/mol vinyl group) at 110° C. for 24 hours. A double porogen system consisting of salt particles (95 wt % of particles are in the range of 105-420 µm) and PEG (600 Da) was used to confer macro-porosity and micro-porosity to the scaffolds respectively. Upon the completion of the curing process, the polymeric pellets underwent a porogen-leaching process via soxhlet extraction for 48 hours. The resulting porous scaffolds were then dried using an ethanol gradient.

TABLE 4

Amino-acid derived biodegradable polycarbonate-urethane porous scaffold formulations with varying DVO:methacrylate ratios

| Scaffold | DVO:methacrylates (molar ratio) | MAA (mol %) | MMA (mol %) |
| --- | --- | --- | --- |
| ReFilx-M10-MA25 | 1:10 | 25 | 75 |
| D-PHI-M20-MA25 | 1:20 | 25 | 75 |
| ReFilx-M21-MA25 | 1:21 | 25 | 75 |
| ReFilx-M30-MA25 | 1:30 | 25 | 75 |
| ReFilx-M40-MA25 | 1:40 | 25 | 75 |
| ReFilx-M50-MA25 | 1:50 | 25 | 75 |
| ReFilx-M60-MA25 | 1:60 | 25 | 75 |
| ReFilx-M70-MA25 | 1:70 | 25 | 75 |
| ReFilx-M80-MA25 | 1:80 | 25 | 75 |
| ReFilx-M90-MA25 | 1:90 | 25 | 75 |
| ReFilx-M100-MA25 | 1:100 | 25 | 75 |

4.3 Mechanical Testing

To assess the mechanical properties of the porous amino-acid derived biodegradable polycarbonate-urethane scaffolds, the compressive modulus was calculated.

Porous amino-acid derived biodegradable polycarbonate-urethane scaffolds were incubated in phosphate-buffered saline (PBS), supplemented with 2% penicillin-streptomycin, for 5 days at 37° C., at which point they were subjected to mechanical testing. Stress-strain data were collected for wet scaffolds (n=5-9) at room temperature in air at a strain rate of 0.017 mm/min. The compressive modulus was calculated from the data.

As shown in Table 56, increasing the amount of methacrylates relative to DVO resulted in a gradual decrease in the compressive modulus. Formulations ReFilx-M80-MA25, ReFilx-M90-MA25, and ReFilx-M100-MA25 could not be measured for compressive strength due to poor structural integrity. Formulation ReFilx-M10-MA25 could not be tested since it could not be processed due to the low viscosity of the monomer mixture.

TABLE 5

Compressive modulus of ReFilx formulations with varying methacrylates:DVO ratios. Formulations highlighted with the red border fall within the useful range of mechanical properties and have not previously been disclosed.

| Scaffold | Compressive Modulus (kPa) |
| --- | --- |
| ReFilx-M10-MA25 | Could not be processed |
| D-PHI-M20-MA25 | 35.1 ± 11.7 |
| ReFilx-M21-MA25 | 34.7 ± 8.6 |
| ReFilx-M30-MA25 | 15.2 ± 3.8 |
| ReFilx-M40-MA25 | 11.0 ± 4.2 |
| ReFilx-M50-MA25 | 5.0 ± 3.1 |
| ReFilx-M60-MA25 | 2.7 ± 1.2 |
| ReFilx-M70-MA25 | 6.7 ± 5.9 |
| ReFilx-M80-MA25 | Poor structural integrity |
| ReFilx-M90-MA25 | Poor structural integrity |
| ReFilx-M100-MA25 | Poor structural integrity |

4.4 Swelling Studies

Swelling studies were performed as outlined in Example 2.2.

Based on gravimetric analysis the ratio of DVO:methacrylates was shown to be directly related to the amount of swelling observed (Table 6). Specifically, it was observed that increasing the amount of methacrylates relative to DVO resulted in greater swelling. Formulations ReFilx-M80-MA25, ReFilx-M90-MA25, and ReFilx-M100-MA25 could not be measured for swelling due to poor structural integrity. Formulation ReFilx-M10-MA25 could not be tested since it could not be processed due to the low viscosity of the monomer mixture.

TABLE 6

Swelling of ReFilx formulations with varying methacrylates:DVO ratios. Formulations highlighted with the red border fall within the useful range of swelling and have not previously been disclosed.

| Scaffold | Compressive Modulus (kPa) |
| --- | --- |
| ReFilx-M10-MA25 | Could not be processed |
| D-PHI-M20-MA25 | 207 ± 34 |
| ReFilx-M21-MA25 | 216 ± 31 |
| ReFilx-M30-MA25 | 345 ± 21 |
| ReFilx-M40-MA25 | 408 ± 21 |
| ReFilx-M50-MA25 | 514 ± 56 |
| ReFilx-M60-MA25 | 675 ± 38 |
| ReFilx-M70-MA25 | 797 ± 113 |
| ReFilx-M80-MA25 | Poor structural integrity |
| ReFilx-M90-MA25 | Poor structural integrity |
| ReFilx-M100-MA25 | Poor structural integrity |

What is claimed is:

1. A biodegradable soft tissue filler comprising a porous scaffold that is the reaction product of:
   a) a divinyl oligomer component that comprises a carbonate-derived divinyl oligomer that is the reaction product of a lysine-derived diisocyanate, a vinyl coupling agent, and a polycarbonate and, optionally, an ether-derived divinyl oligomer, wherein the ether-derived divinyl oligomer is the reaction product of a lysine-derived diisocyanate, a vinyl coupling agent, and an ether;
   b) at least one anionic monomer; and
   c) at least one hydrophobic monomer;
   wherein
   the molar ratio of (a): (b+c) is between about 1:21 and about 1:30;
   wherein the soft tissue filler has a porosity of >75%; and
   wherein the soft tissue filler has a compressive moduli of between about 1 kPa and about 50 kPa.

2. The soft tissue filler of claim 1, wherein the anionic monomer is methacrylic acid and/or the hydrophobic monomer is methyl methacrylate.

3. The soft tissue filler of claim 1, wherein component (a) is a carbonate-derived divinyl oligomer and wherein (a), (b) and (c) are reacted in the presence of at least one porogen (d) and wherein (a), (b) and (c) combined comprise between about 5 wt % and 20 wt % of the reaction mixture and (d) comprises between 80 and about 95 by wt % of the reaction mixture.

4. The soft tissue filler of claim 1 or 2, wherein the divinyl oligomer component comprises the carbonate-derived divinyl oligomer and the ether-derived divinyl oligomer.

5. The soft tissue filler of claim 4, wherein (a), (b) and (c) are reacted in the presence of at least one porogen (d) and wherein (a), (b) and (c) combined comprise between about 5 wt % up to 25 wt % of the reaction mixture and (d) comprises between >75 to about 95 by wt % of the reaction mixture.

6. The soft tissue filler of claim 5, wherein (d) comprises between 80 and about 95 by wt % of the reaction mixture.

7. The soft tissue filler of claim 4, wherein the molar ratio of the carbonate-derived divinyl oligomer to ether-derived divinyl oligomer is between about 1:100 to 50:50.

8. The soft tissue filler of claim 1, wherein the soft tissue filler has a compressive moduli of between about 10 kPa and about 40 kPa.

9. The soft tissue filler of claim 1, wherein the soft tissue filler demonstrates a swelling of between about 100% and about 300%.

10. The soft tissue filler of claim 1 further comprising one or more additives selected from antioxidants, cross-linkers, plasticizers or nucleating agents.

11. The soft tissue filler of claim 1, wherein the soft tissue filler is in the form of a pellet.

12. The soft tissue filler of claim 11, wherein the pellet has a dry volume of between 0.1 mm$^3$ and 100 mm$^3$.

13. The soft tissue filler of claim 11, further comprising one or more of a therapeutic agent, a bioactive agent and cells.

14. The soft tissue filler of claim 1 wherein the soft tissue filler is injectable.

15. The soft tissue filler according to claim 1 wherein the soft tissue filler is a breast tissue filler.

16. A method of repairing a soft tissue defect in a patient in need thereof comprising implanting a soft tissue filler according to claim 1 at the site of the soft tissue defect.

17. The method of claim 16 further comprising hydrating the soft tissue filler prior to implantation.

18. The method of claim 16 wherein the soft tissue defect is in connective and/or fatty and/or fibrous soft tissue.

19. The method of claim 18 wherein the soft tissue defect is in the breast.

20. The method of claim 19, wherein the soft tissue defect is the result of a lumpectomy or breast tissue biopsy.

21. A soft tissue filler comprising an amino-acid derived biodegradable polycarbonate-urethane scaffold having a porosity of between about 80% and about 95%, a compressive moduli of between about 1 kPa and about 50 kPa, a swelling capacity of between about 100% and about 300%, and a dry volume of 50 mm$^3$±25 mm$^3$.

22. The soft tissue filler of claim 7, wherein the molar ratio of the carbonate-derived divinvl oligomer to ether-derived divinyl oligomer is about 10:90.

23. The soft tissue filler of claim 12, wherein the pellet has a dry volume of 50-60 mm$^3$±10 mm$^3$.

* * * * *